US007358083B1

(12) United States Patent
Sorensen et al.

(10) Patent No.: US 7,358,083 B1
(45) Date of Patent: Apr. 15, 2008

(54) FOOD-GRADE CLONING VECTOR AND THEIR USE IN LACTIC ACID BACTERIA

(75) Inventors: Kim Sorensen, Farum (DK); Rasmus Larsen, Copenhagen (DK); Eric Johansen, Horsholm (DK)

(73) Assignee: Chr. Hansen A/S, Horsholm (DK)

( * ) Notice: Subject to any disclaimer, the term of this patent is extended or adjusted under 35 U.S.C. 154(b) by 0 days.

(21) Appl. No.: 09/673,617

(22) PCT Filed: Apr. 14, 1999

(86) PCT No.: PCT/DK99/00209

§ 371 (c)(1),
(2), (4) Date: Jan. 25, 2001

(87) PCT Pub. No.: WO99/54488

PCT Pub. Date: Oct. 28, 1999

Related U.S. Application Data

(60) Provisional application No. 60/082,555, filed on Apr. 21, 1998.

(30) Foreign Application Priority Data

Apr. 21, 1998 (DK) .................................. 0551/98

(51) Int. Cl.
*C12N 15/74* (2006.01)
*C12N 1/21* (2006.01)
*C12N 15/68* (2006.01)
*A23C 9/123* (2006.01)

(52) U.S. Cl. ............................... 435/320.1; 435/252.3; 435/252.9; 435/471; 435/476; 435/481; 426/42; 426/34

(58) Field of Classification Search .............. 435/320.1, 435/69.1, 252.3, 252.9; 536/23.1
See application file for complete search history.

(56) References Cited

U.S. PATENT DOCUMENTS 5,627,072 A 5/1997 Leenhouts et al. ........ 435/320.1
5,866,385 A * 2/1999 Dickely et al. ................ 435/6

FOREIGN PATENT DOCUMENTS

| WO | 90/00599 | 1/1990 |
| WO | 91/09131 | 6/1991 |
| WO | 94/16086 | 7/1994 |
| WO | 95/10621 | 4/1995 |

OTHER PUBLICATIONS

Paal Skytt Andersen et al., "Sequence Analysis and Identification of the pyrKDbF Operon *Lactococcus lactis* including a Novel Gene, pyrK, Involved in Pyrimidine Biosynthesis.", Journal of Bacteriology, pp. 5005-5012, Aug. 1995.
Michael R. Cancilla et al., "*Lactococcus lactis* glyceraldehyde-3-phosphate dehydrogenase gene, gap: further evidence for strongly biased codon usage in glycolytic pathway genes.", Microbiology, vol. 141, pp. 1027-1036, 1995.
M. Demerec et al., "A Proposal For A Uniform Nomenclature In Bacterial Genetics.", Genetics, vol. 54, pp. 61-76, Jul. 1966.
Francoise Dickely et al., "Isolation of *Lactococcus lactis* nonsense supressors and construction of a food-grade cloning vector.", Molecular Microbiology, vol. 15, No. 5, pp. 839-847, 1995.
Gudmundur Eggertsson et al., "Transfer Ribonucleic Acid-Mediated Suppression of Termination Codons in *Escherichia coli*.", Microbiological Reviews, pp. 354-374, Sep. 1988.
Michael J. Gasson, "Plasmid Complements of *Streptococcus lactis* NCDO 712 and Other Lactic *Streptococci* After Protoplast-Induced Curing.", Journal of Bacteriology, vol. 154, No. 1, pp. 1-9, Apr. 1983.
Helge Holo et al., "High-Frequency Transformation, by Electroporation, of *Lactococcus lactis* subsp. cremoris Grown with Glycine in Osmotically Stabilized Media.", Applied and Environment Microbiology, vol. 55, No. 12, pp. 3119-3123, Dec. 1989.
E. Johansen et al., "Nonsense Suppression in *Lactococcus lactis*: Construction of a <<Food-Grade>> Cloning Vector.", Developments in Biological Standardization, vol. 85, pp. 531-534, 1995, XP-002085666.
Oscar P. Kuipers et al., "Characterization of the nisin gene cluster nisABTCIPR of *Lactococcus lactis* Requirement of expression of the nisA and nisI gene for development of immunity.", European Journal of Biochemistry, vol. 216, pp. 281-291, Aug. 1993, XP-002041580.
Eric. Johansen et al., "Characterization of Leuconostoc Isolates from Commercial Mixed Strain Mesophilic Starter Cultures.", J. Dairy Sci. vol. 75, pp. 1186-1191, 1992.
J. Lawrence Marsh et al., "The pIC plasmid and phage vectors with versatile cloning sites for recombinant selection by insertional inactivation.", Gene, vol. 32, pp. 481-485, 1984.
Morten L. Pedersen et al., "Genetic analysis of the minimal replicon of the *Lactococcus lactis* subsp. Lactis blovar diacetylactis citrate plasmid.", Mol. Gen. Genet., vol. 244, pp. 374-382, 1994.
Henry V. Huang et al., "Improved Suppressor tRNA Cloning Vectors and Plasmid-Phage Recombination.", Vectors (A Survey of Molecular Cloning Vectors and Their Uses), Chapter 14, pp. 269-283.
Kim I. Sorensen et al., "A Food-Grade Cloning system for Industrial Strains of *Lactococcus lactis*.", Applied and Environmental Microbiology, vol. 66, No. 4, pp. 1253-1258, Apr. 2000.
Morten L. Pedersen et al., "Genetic analysis of the minimal replicon of the *Lactococcus lactis* subsp. Lactis blovar diacetylactis citrate plasmid.", Mol. Gen. Genet., vol. 244, pp. 374-382, 1994.
Henry V. Huang et al., "Improved Suppressor tRNA Cloning Vectors and Plasmid-Phage Recombination.", Vectors (A Survey of Molecular Cloning Vectors and Their Uses), Chapter 14, pp. 269-283, 1988.
Kim I. Sorensen et al., "A Food-Grade Cloning system for Industrial Strains of *Lactococcus lactis*.", Applied and Environmental Microbiology, vol. 66, No. 4, pp. 1253-1258, Apr. 2000.

\* cited by examiner

*Primary Examiner*—Sumesh Kaushal
*Assistant Examiner*—Michael Burkhart
(74) *Attorney, Agent, or Firm*—Foley & Lardner LLP

(57) ABSTRACT

Novel food-grade cloning vectors comprising a nonsense mutation suppressor-encoding gene, which vector, when it is present in a lactic acid bacterial strain, permits such a strain to have an industrially appropriate growth rate and metabolic activity. The cloning vectors are useful when present in lactic acid bacteria used as starter cultures in the preparation of food or feed products, or a dairy flavor.

4 Claims, 10 Drawing Sheets

```
  1 TGATTTTATTATTAGCTAAAATTACTGACAGCCTGTTTAATCATTCTGTCAGTAAAATGC  60
 61 GACCAAAGCGAGCATTTTATCCATAGCTAAAAGAATTGTCAGCGGAGCTGATAATTCTCT 120
121 CGTTCGTTAGCGACCAAAGCGAGCATTTTATGGATAGCTAAAAGAATTGTCATCAAAGCT 160
181 GATAATTCTGTCATTAAATATTTAGAAAAAGGAAGTAGAAAAAATGCAAGAAAATAGACC 240
                                           M  Q  E  N  R  P  -
241 TGTCATTGCCCTTGATTTCCCTGAATTCTCAGACGTAAAAGATTTTCTCGAAAAATTTGA 300
     V  I  A  L  D  F  P  E  F  S  D  V  K  D  F  L  E  K  F  D  -
301 CCCGTCAGAACAATTGTATATTAAACTAGGAATGGAACTTTTTTACACGGCTGGGCCCCA 360
     P  S  E  Q  L  Y  I  K  L  G  M  E  L  F  Y  T  A  G  P  Q  -
361 AGTCGTTTACTATGTAAAATCGCTCGGCCACAGTGTATTCCTTGATTTAAAACTCCATGA 420
     V  V  Y  Y  V  K  S  L  G  H  S  V  F  L  D  L  K  L  H  D  -
421 TATTCCAAACACCGTTGAATCCTCAATGCGTGTTTTAGCACGTTTGGGATTGGATATGGT 480
     I  P  N  T  V  E  S  S  M  R  V  L  A  R  L  G  L  D  M  V  -
481 TAATGTTCACGCCGCTGGTGGTGTTGAAATGATGGTTGCAGCTAAACGCGGTTTAGAGGC 540
     N  V  H  A  A  G  G  V  E  M  M  V  A  A  K  R  G  L  E  A  -
541 TGGAACGCCAGTTGGACGGCAAAGGCCAAAATTAATTGCGGTCACACAATTAACCTCAAC 600
     G  T  P  V  G  R  Q  R  P  K  L  I  A  V  T  Q  L  T  S  T  -
601 TTCTGAGAAAATTATGCAAAATGACCAAAAAATTATGACTAGTCTTGAAGAATCGGTTAT 660
     S  E  K  I  M  Q  N  D  Q  K  I  M  T  S  L  E  E  S  V  I  -
661 TAATTACGCACAAAAAACCGCTCAAGCAGGACTTGACGGTGTCGTTTGTTCGGCACATGA 720
     N  Y  A  Q  K  T  A  Q  A  G  L  D  G  V  V  C  S  A  H  E  -
721 AGTTGAAAAAATTAAAGCAGCGACATCGAAAGAATTCATTTGTCTCACACCAGGAATTCG 780
     V  E  K  I  K  A  A  T  S  K  E  F  I  C  L  T  P  G  I  R  -
781 CCCAGAAGGTGCAAGTAAAGGCGACCAAAAACGAGTAATGACACCTAAAGAAGCAAGAAC 840
     P  E  G  A  S  K  G  D  Q  K  R  V  M  T  P  K  E  A  R  T  -
841 AATTGGTTCAGATTATATTGTTGTCGGCCGTCCAATTACCCAAGCAAAAGATCCAGTAGC 900
     I  G  S  D  Y  I  V  V  G  R  P  I  T  Q  A  K  D  P  V  A  -
901 TAGCTATCATGCGATAAAAGCAGAATGGAATCAATAA 937
     S  Y  H  A  I  K  A  E  W  N  Q  *
```

Fig. 8

FOOD-GRADE CLONING VECTOR AND THEIR USE IN LACTIC ACID BACTERIA

FIELD OF INVENTION

The present invention relates to the field of lactic acid bacterial starter cultures and in particular there is provided a food-grade vector comprising a nonsense mutation suppressor-encoding gene which vector, when it is present in a lactic acid bacterial strain, permits such a strain to have an industrially appropriate growth rate and metabolic activity.

TECHNICAL BACKGROUND AND PRIOR ART

Lactic acid bacteria are used extensively as starter cultures in the food industry in the manufacturing of fermented products including milk products such as e.g. yoghurt and cheese, meat products, bakery products, wine and vegetable products. *Lactococcus* species including *Lactococcus lactis* are among the most commonly used lactic acid bacteria in dairy starter cultures. However, several other lactic acid bacteria such as *Leuconostoc* species, *Pediococcus* species, *Lactobacillus* species and *Streptococcus* species are also commonly used in food starter cultures.

A significant role of lactic acid bacteria is to render the fermented products microbiologically stable and to improve the taste and palatability of these products. It is generally recognised that genes, the expression of which are important to ensure that the addition of lactic acid bacteria to a starting material results in the desired fermentation effect, are found naturally or can be inserted on extrachromosomal DNA vectors including plasmids.

However, DNA vectors may be unstable, resulting in their loss from the cells. Accordingly, it is of pertinent industrial interest to provide vectors which are stably maintained in lactic acid bacterial starter cultures.

Presently used methods of stably maintaining (stabilising) vectors in a host cell include insertion of relatively large DNA sequences such e.g. antibiotic or bacteriocin resistance genes into the cell. In the art, such genes are also referred to as selection markers. However, it is well-known that the insertion of large DNA sequences involves the risk that other sequences are deleted from the vector. Furthermore, the use of resistance genes for maintaining the plasmid in the host cell implies that antibiotics or bacteriocins must be present in the cultivation medium. This is undesirable in the manufacturing of food and feed products. In addition, it is undesirable that live bacteria comprising antibiotic resistance genes are present in food products as such genes may be transferable to the indigenous gastro-intestinal microflora.

Consequently, there have been reported several attempts to develop so-called food-grade cloning vectors. In the present context, the term "food-grade" indicates that the vector consists essentially of DNA of lactic acid bacterial origin.

WO 91/09131 discloses a vector essentially consisting of lactic acid bacterial DNA wherein a gene coding for the bacteriocin nisin is used as a selectable marker. However, the selection of such a vector still requires that a selective compound is added to the cultivation medium.

As an alternative approach, it has been suggested to use vectors carrying a gene coding for a gene product that suppresses nonsense mutations in lactic acid bacteria.

In the in vivo synthesis of proteins occurring in the ribosomes, mRNA is translated into polypeptide chains. However, the mRNA codons do not directly recognise the amino acids that they specify in the way that an enzyme recognises a substrate. Translation uses "adaptor" molecules that recognise both an amino acid and a triplet group of nucleotide bases (a codon). These adaptors consist of a set of small RNA molecules known as transfer RNAs (or tRNAs), each of which is only 70 to 90 nucleotides in length. Such tRNA molecules contain unpaired nucleotide residues comprising a CCA triplet at one end of the molecule and, in a central loop, a triplet of varying sequence forming the so-called anticodon that can base-pair to a complementary triplet in the mRNA molecule, while the CCA triplet at the free 3' end of the molecule is attached covalently to a specific amino acid.

The three nucleotide triplets UAG (amber codon), UGA (opal codon) and UM (ochre codon) do not code for an amino acid. These signals termed stop codons or "nonsense" codons, are involved in polypeptide chain termination. During translation, two protein factors (R1 and R2) recognise these triplets and effect release of the polypeptide chain from the ribosome-mRNA-tRNA complex.

Occasionally a mutation occurs in a cell resulting in a nonsense codon appearing within a gene, causing premature chain termination and the production of a protein fragment. Such fragments rarely have enzymatic activity.

The effect of such a nonsense mutation can be reversed or suppressed by a second mutation in a gene coding for a tRNA which results in the synthesis of an altered tRNA molecule. Such an altered tRNA recognises a nonsense codon and inserts an amino acid at that point in the polypeptide chain. The mutated tRNA-encoding gene is termed a suppressor gene and the altered nonsense mutation-suppressing tRNA which it encodes is generally referred to as a nonsense or termination suppressor. Such termination suppressors may be derived by single, double or triple base substitutions in the anticodon region of the tRNA.

Most mutations in a tRNA-encoding gene leading to the formation of a nonsense suppressor are located in the anticodon triplet and alter it to CUA, UUA or UCA. Such suppressors may be referred to as amber, ochre and opal suppressors, respectively. Following the rules of nomenclature of Demerec et al., 1966 which was suggested for termination (nonsense) suppressors in *E. coli* the symbol "sup" and assigned capital letters as gene designations, e.g. supB, supC or supZ, are used herein also to designate suppressor genes in lactic acid bacteria.

In Dickely et al. 1995, Johansen et al. 1995 and WO 95/10621 are disclosed plasmids containing a gene coding for a tRNA that is a suppressor for a nonsense mutation where the suppressor gene will function as a selectable marker when the nonsense mutation in the host strain for the plasmid is one which, in the absence of a corresponding suppressor gene, will render the host strain incapable of growing in a particular environments, such as e.g. milk or other food or feed products. The genes coding for suppressor tRNA are small and can be inserted without causing deletions of desired genes. Also, homologous recombination will not occur between supD and the chromosomal tRNA genes due to the small size.

The construction of the vector pAK89.1 that comprises a supD suppressor is described in Dickely et al. 1995 and WO 95/10621. However, this cloning vector contains a gene coding for erythromycin resistance and thus is not a food-grade vector.

Dickely et al. 1995 and WO 95/10621 disclose food-grade vectors based on the *Lactococcus lactis* derived nonsense suppressor, supB, as a selection marker. However, these vectors, pFG1 and pFG1.1, cause growth inhibition when present in host cells. It has also been found that these particular vectors, when present in lactic acid bacterial strains, are unstable and that the acidification rate of the host cells in milk is reduced as compared to wildtype strains and therefore these vectors are not suitable in industrial processes.

Accordingly, the prior art is not aware of nonsense suppressor containing food-grade vectors that are stably maintained in lactic acid bacterial strains and which do not adversely affect the growth and metabolic activity of the host strains.

The present invention provides a food-grade vector, comprising as the selection marker a nonsense suppressor gene. It was surprisingly found, that the vector, when it is present in a lactic acid bacterial strain comprising a nonsense mutation suppressible by the suppressor, substantially does not cause growth inhibition and permits the strain to acidify milk at essentially the same rate as that of the same strain not containing the vector.

SUMMARY OF THE INVENTION

Accordingly, the present invention relates in a first aspect to a recombinant vector consisting essentially of lactic acid bacterial DNA, the vector comprising a gene coding for a tRNA comprising an amber suppressor and a replicon making the vector capable of replicating in a lactic acid bacterium, the vector having at least one of the following characteristics:

(i) when it is present in *Lactococcus lactis* strain FA4-1-1 deposited under the accession No. DSM 12086 having an amber mutation in the pyrF gene that is suppressible by the suppressor, it permits said strain to grow at 30° C. at a doubling time of at the most 100 minutes in a minimal medium not containing pyrimidine sources; and/or (ii) when it is present in a strain of *Lactococcus lactis* FH CY-1 that has an amber mutation in the pyrF gene (strain CHCC4146, DSM 12109), said amber mutation being suppressible by the suppressor, it permits the strain to acidify milk under identical conditions at essentially the same rate of that of the parent strain (FH CY-1) deposited under the accession No. DSM 12087;

and/or (iii) it permits the *Lactococcus lactis* FA4-1-1 strain (DSM 12086) to grow at 30° C. in a minimal medium not containing pyrimidine sources at a doubling time which is less than that for the *Lactococcus lactis* strain DN209 transformed with the vector pFG1.1 deposited under the accession No. DSM 12088, the pFG1.1 vector comprising a gene coding for a suppressor that is capable of suppressing the nonsense mutation in the DN209 strain, the transformed DN209 strain growing under conditions identical to those for the FA4-1-1 strain.

The present invention also pertains to a lactic acid bacterium comprising a vector according to the invention, the lactic acid bacterium possibly comprising an amber mutation being suppressible by the nonsense amber suppressor.

In a further aspect, the invention relates to an isolated pure culture of a lactic acid bacterium according to the invention, to a composition comprising such an isolated pure culture, and a carrier, and to the use of such a composition as a starter culture in the preparation of a product selected from the group consisting of a dairy flavour, a product for cheese flavouring, a food product and a feed product.

In one interesting aspect, the invention relates to a method of stably maintaining a vector according to the invention in lactic acid bacterial host cells growing in a particular environment, comprising providing said host cells as nonsense mutant cells having lost the capability of growing in said environment, and transformed with a plasmid according to the invention containing a nonsense suppressor gene encoding a gene product restoring the capability of the nonsense mutant cells to grow in said environment whereby, if the plasmid is lost from the lactic acid bacterial cells, the cells will not grow.

DETAILED DISCLOSURE OF THE INVENTION

Thus, it is an important objective of the present invention to provide a recombinant vector consisting essentially of lactic acid bacterial DNA, the vector comprising a gene coding for a tRNA comprising an amber suppressor and a replicon making the vector capable of replicating in a lactic acid bacterium and having at least one of the characteristics (i) to (iii) as mentioned above.

As used herein, the term "vector" is used interchangeable with the terms "recombinant vector", "cloning vector" and "expression vector", and relates to any DNA molecule that acts as an intermediate carrier into which a gene or a DNA segment is inserted for introduction into bacterial or other cells for amplification. Such intermediate carriers include DNA fragments or subsequences, plasmids, cosmids, bacteriophages and transposons.

When used herein, the term "lactic acid bacterium" designates a group of bacteria having as a common characteristic the capability to produce lactic acid from sugars. The majority of the species belonging to this group can be characterised as gram-positive, catalase-negative, microaerophilic or anaerobic bacteria which may be cocci or rods. The anaerobic genus *Bifidobacterium* is also generally included in the group of lactic acid bacteria.

The recombinant vector according to the invention consists essentially of DNA of lactic acid bacterial origin including DNA isolated from vectors or other replicons having the lactic acid bacterium as their natural host organism. In the art, such vectors are, as it is mentioned above, also referred to as being "food grade" vectors, since it is generally considered that the use of such vectors may be allowable by relevant governmental authorities for use in food manufacturing.

In the present context, the expression "amber mutation" relates to a mutation in a cell resulting in the nonsense codon UAG appearing within a coding sequence of a gene resulting in premature chain termination. The effect of such amber mutations can be reversed or suppressed by an "amber suppressor" i.e. a tRNA comprising an altered anticodon, CUA, which only recognises amber mutations and which is the result of at least one change of nucleotide in a gene coding for a tRNA anticodon (Eggertson et al., 1988).

As mentioned above, one characteristic of the vector of the present invention is that it, when it is present in *Lactococcus lactis* strain FA4-1-1 (DSM 12086) having an amber mutation in the pyrF gene that is suppressible by the amber suppressor, permits said strain to grow at 30° C. at a doubling time of at the most 100 minutes in a medium not containing pyrimidine sources. In preferred embodiments the vector permits the above strain to grow at a doubling time of at the most 95 minutes such as at the most 90 minutes including at the most 85 minutes.

It will be understood, that an amber mutation in a pyr gene of a lactic acid bacterial cell causes the cell to lose its capability to grow in a medium, like e.g. milk, which does not contain pyrimidines. Such an auxotrophic mutant will only be able to grow in the absence of pyrimidine precursor if the vector of the present invention is present in the host cell. Thus, the amber suppressor restores the capability of the cell to grow in such a medium.

As it is also mentioned above, it is of industrial interest that a vector according to the invention, when it is present in a lactic acid bacterial strain does not cause any substantial growth inhibition of the host strain. Thus, the vector, when it is present in the *Lactococcus lactis* strain CHCC4146 (DSM 12109), permits this strain to acidify milk at essentially the same rate as that of the same strain not containing an amber suppressor.

The term "milk" as used herein is intended to mean any type of milk or milkcomponent which does not contain the precursors for the synthesis of pyrimidine nucleotides including e.g. cow's milk, human milk, buffalo milk, goat's milk, sheep's milk, or whey.

suppressor may be one which results from at least one nucleotide change in a gene coding for a tRNA anticodon resulting in the altered tRNA anticodon CUA. In useful embodiments the suppressor is a supD, supE, supF, supP, supU or a supZ suppressor.

In other specific embodiments, the amber suppressor may be derived by double or triple base substitutions in the anticodon region of the tRNA.

The DNA sequence comprising the tRNA encoding suppressor gene is preferably a small sequence such as a sequence in the range of 0.05 to 10 kb, more preferably in the range of 0.1 to 5.1 kb, such as e.g. 3.2, 1.1 or 0.25 kb. As an example, the DNA sequence coding for such a tRNA may be the following (SEQ ID NO:1):

```
 1 GGAGCCATGG CAGAGTGGTA ATGCAACGGA CTCTAAATCC GTCGAACCGT

51 GTAAAGCGGC GCAGGGGTTC AAATCCCCTT GACTCCTTA
```

Evidently, the above-mentioned acidification of milk will result in essentially the same pH decrease in the medium inoculated with the respective strains. However, it is contemplated that with other host strains, the acidification rate may be insignificantly reduced by the presence of the vector according to the invention. Accordingly, the expression "at essentially the same acidification rate" includes that in comparative acidification experiments, the ΔpH after about 3 hours of cultivation is at the most 1.0 such as at the most 0.5 including at the most 0.2 such as e.g. at the most 0.1.

It is another objective of the invention to provide recombinant food-grade vectors that do no inhibit growth rate of lactic bacterial host cells. Thus, as it is also shown in the below examples, the vector of the present invention permits a host cell such as *Lactococcus lactis* FA4-1-1 strain to grow at 30° C. in minimal medium at a doubling time which is shorter than that for the strain DN209 transformed with the vector pFG1.1 (DSM 12088). In useful embodiments the doubling time of a host cell transformed with the vector of the invention is at least 5 minutes shorter than that of the strain DN209 transformed with the vector pFG1.1, such as at least 10 minutes shorter e.g. at least 15 minutes shorter or even at least 20 minutes shorter.

In accordance with the invention, the recombinant vector has at least one of the above characteristics (i) to (iii). However, it is preferred that the vector has at least two of such characteristics and most preferably all of these characteristics.

The suppressor gene comprised in the recombinant vector is typically derived from a lactic acid bacterial cell which is subjected to a mutagenisation treatment followed by selecting mutants suppressing an amber nonsense mutation e.g. such as it is described by Dickely et al. 1995 and isolating a DNA sequence comprising the mutated suppressor gene. However, the suppressor gene comprised in the recombinant vector can be provided by selecting a spontaneously occurring mutant in accordance with the screening method as described above.

Alternatively, it is possible to construct a tRNA gene coding for the suppressor by conventional DNA synthesis methods or by in vivo mutagenesis of isolated genes. Normally, the mutated tRNA-encoding gene is derived from the chromosome of the source strain. Preferably, the suppressor gene encodes a tRNA with an anticodon selectively recognising amber codons, i.e. an amber suppressor. The nonsense In one interesting embodiment of the present invention, the vector is one wherein the gene coding for a nonsense suppressor is under the control of a regulatable promoter. As used herein, the term "regulatable promoter" is used to describe a promoter sequence possibly including regulatory sequences for the promoter, which promoter is regulatable by one or more factors occurring during the growth of a host cell comprising the recombinant vector. Such factors include the pH and/or the arginine content of the growth medium, the growth temperature, a temperature shift eliciting the expression of heat shock genes, the composition of the growth medium including the ionic strength/NaCl content and the growth phase/growth rate of the lactic acid bacterium. Such a regulatable promoter may be the native promoter or it may be an inserted promoter not naturally related to the suppressor gene either isolated from the lactic acid bacterial species or it may be a heterologous promoter sequence, i.e. a sequence derived from a different lactic acid bacterial species.

A promoter sequence as defined above may comprise further sequences whereby the promoter becomes regulated by a stochastic event. Such a regulation may e.g. be useful in lactic acid bacterial cultures for which it may be advantageous to have a gradually decreasing activity of the suppressor gene under control of the promoter sequence. Such further sequences may e.g. be sequences, the presence of which results in a recombinational excision of the promoter or of genes coding for substances which are positively needed for the promoter function.

In accordance with the present invention, the vector is typically constructed by combining a DNA sequence comprising a suppressor gene which is functional in a lactic acid bacterium and a replicon capable of replicating in a lactic acid bacterium. In a useful embodiment the replicon is from a *Lactococcus lactis* plasmid. More specifically, the replicon is derived from the *Lactococcus lactis* subsp. *lactis* biovar. diacetylactis citrate plasmid pCT1138 or the *Lactococcus lactis* plasmid pIL2608 such as it is described in the following examples.

For a vector construct as described above to be useful as a cloning vector it is provided with at least one restriction site. Preferably, the restriction site(s) is/are unique sites. In useful embodiments, the vector comprises at least one DNA sequence containing multiple cloning sites.

Examples of vectors, which are encompassed by the present invention, are the multi-copy vectors pFG100 and pFG200 as described in the examples.

In addition, the present invention encompasses mutants, variants or derivatives having essentially the characteristics of the vectors pFG100 and pFG200. In this context, the terms "mutant", "variant" or "derivative" refers to any modification of the DNA sequence of the above vectors including substitution, addition or deletion of nucleotides in the suppressor gene, the replicon, any regulatory DNA sequences or any other sequence of the vector, that substantially does not affect the characteristics of the modified vector, relative to the parent vector.

Preferably, vectors as described above have a size allowing for the insertion of desirable genes. Accordingly, a suitably sized vector as defined herein has a size which is in the range of 0.5 to 20 kb, although larger vectors may also be used. In preferred embodiments the vector has a size in the range of 1 to 10 kb, such as in the range of 2 to 5 kb.

The vector according to the invention may further comprise an inserted gene coding for a desired gene product. In this context, interesting desired gene products include genes coding for enzymes which have an advantageous effect on the quality of a food product, the manufacturing or preservation of which includes the addition of viable lactic acid bacterial cultures as it has been described above. Thus, such genes inserted into the vector may code for a peptidase, including lysine-aminopeptidase, glutamyl-aminopeptidase, cysteine-aminopeptidase, iminopeptidase, X-prolyl-dipeptidyl aminopeptidase, endopeptidase, dipeptidase or tripeptidase.

In the present context, other interesting gene products include lipases, proteases, nucleases and enzymes which are involved in the carbohydrate metabolism of the host bacterium. Inserted genes may also be prokaryotic or eucaryotic genes isolated from non-lactic acid bacterial species. Additionally, one useful gene product includes a gene product which is involved in nisin synthesis or nisin resistance.

In accordance with the invention, an interesting gene product includes a gene product conferring bacteriophage resistance to the lactic acid bacterial host cell. In another useful embodiment the vector according to the invention comprises a gene coding for a bacteriophage lysine, which in a specific embodiment is derived from the bacteriophage ØvML3 contained in the strain DN209/pFG7 deposited with the Deutsche Sammlung von Mikroorganismen und Zellkulturen, Mascheroder Weg, 1b, D-38124 Braunschweig on 6 Apr. 1998 under the accession No. DSM 12089. In a further specific embodiment the vector according to the invention is a theta-replicating vector.

As it mentioned above, it is a further object of the invention to provide food-grade vectors which can be stably maintained in a lactic acid bacterial host cell. Accordingly, there is preferably substantially no loss of the vector when the host strain is grown for at least 20 generations, including at least 35 generations such as at least 50 generations or even at least 100 generations in a medium wherein a host cell not containing the vector is not capable of growing. Thus, when the host cell comprises a nonsense mutation conferring auxotrophy e.g. with respect to amino acid or nucleotide precursor compounds, such as purine or pyrimidine precursors, the vector will be selected (stabilised) in a medium not containing such precursors.

The invention provides in a further aspect a lactic acid bacterium comprising a vector according to the invention. Normally, the bacterium also comprises an amber mutation being suppressible by the nonsense amber suppressor. Such a gene coding for the nonsense mutation may be located on a replicon different from the one containing the gene coding for a nonsense suppressor, e.g. on the chromosome, on a plasmid or it may be incorporated in the cell as a prophage.

In certain preferred embodiments, the lactic acid bacterium of the present invention comprises a suppressor which is capable of suppressing a nonsense mutation which, in the absence of the nonsense suppressor, confers auxotrophy. Such a nonsense mutation may e.g. be in a gene involved in the synthesis of pyrimidine nucleotides from their precursors in which case the lactic acid bacterium is a nonsense pyr mutant such as a pyrF$^-$ mutant.

The lactic acid bacterium of the invention can be any lactic acid bacterium selected from the group consisting of a *Lactococcus* sp., *Streptococcus* sp., *Lactobacillus* sp., *Leuconostoc* sp., *Pediococcus* sp. and *Bifidobacterium* sp. One preferred species is *Lactococcus lactis* including *Lactococcus lactis* subsp. *lactis*. Examples of strains belonging to the latter species include strain FA4-1-1 containing pFG100, deposited under the accession No. DSM 12091 and *Lactococcus lactis* subsp. *lactis* strain CHCC4146 containing pFG200, deposited under the accession No. DSM 12108.

In a still further aspect, the invention relates to an isolated pure culture of a lactic acid bacterium as defined above, the expression "pure culture" indicating that the culture contains a biomass of one single isolate of a lactic acid bacterial species, i.e. a clone originating in principle from one cell. Such a pure culture may be provided as a liquid cell suspension or as frozen or freeze-dried preparation. Preferably the pure culture is in a concentrate of cells obtained by separation e.g. by centrifugation or filtration using conventional techniques.

In yet a further aspect, the present invention relates to a composition comprising an isolated pure culture of a lactic acid bacterium as defined above, and a micro-biologically acceptable carrier. It may be preferred that such a composition contains at least $10^5$ colony forming units (CFUs) of the bacterium such as at least $10^7$ or at least $10^9$ CFUs per g. Suitable carriers substances include nutrients such as an assimilable carbohydrate or a nitrogen source, which can be utilised readily by the lactic acid bacterium. Typically, such a composition is provided in the form of a frozen or freeze-dried composition. In the latter case, the composition may contain cryoprotective compounds.

The composition may, in accordance with the invention, comprise two or more different species of lactic acid bacteria or two or more strains of the same species. It is common in the production of food products, where lactic acid bacterial starter cultures are used, to apply mixed cultures, i.e. cultures comprising a multiplicity of strains. As an example hereof it can be mentioned that a mixed culture of *Lactobacillus bulgaricus* and *Streptococcus thermophilus* is typically used in the production of yoghurt. In other dairy products a mixed culture of *Bifidobacterium bifidum* and *Lactobacillus acidophilus* are used.

In further aspects, the invention relates to the use of the above composition as a starter culture in the preparation of a food product such as e.g. a dairy product, a vegetable product, a meat product, a bakery product or a wine product, and its use in the production of an animal feed such as silage, from e.g. grass, cereal, peas, alfalfa or sugar-beet leaf, where starter cultures are inoculated in the feed crop to be ensued in order to obtain a preservation hereof, or in protein rich animal waste products such as slaughtering offal and fish offal, also with the aims of preserving this offal for animal feeding purposes. Yet another significant application of lactic acid bacterial cultures according to the present invention is the use of such cultures as so-called probiotics. By the term "probiotic" is in the present context understood a microbial culture which, when ingested in the form of viable cells by humans or animals, confers an improved health condition, e.g. by suppressing harmful microorganisms in the gastrointestinal tract, by enhancing the immune system or by contributing to the digestion of nutrients.

In another specific embodiment, the above composition is used as a starter culture in the preparation of a dairy flavour used for e.g. flavouring of butter, margarine, spreads, cereal products or pop-corn, or for a product for cheese flavouring.

In accordance with the present invention there is also provided a method of stably maintaining a vector of the present invention in lactic acid bacterial host cells growing in a particular environment, comprising providing said host cells as nonsense mutant cells having lost the capability of growing in said environment, and transformed with a vector according to the invention containing a nonsense suppressor gene encoding a gene product restoring the capability of the nonsense mutant cells to grow in said environment whereby, if the vector is lost from the lactic acid bacterial cells, the cells will not grow.

In suitable embodiments of the invention, the lactic acid bacterial host cells harbouring the vector to be stably maintained have a nonsense mutation in one or more genes conferring auxotrophy to the cells whereby the cells have lost their capability to grow in the particular environment due to a lack herein of an essential nutrient substance which cannot be synthesised by the nonsense mutant cells.

As one example, the nonsense mutation may be one which causes the host cells to lose the capability to grow in a medium which does not contain pyrimidines.

Accordingly, the suppressor gene of the vector functions as a selective marker for the lactic acid bacterial host cells. In the present context, the term "a selective marker" is used to designate a gene coding for a product which renders lactic acid bacterial cells unable to grow if the vector to be maintained is lost from the cells.

Thus, in accordance with the invention, auxothrophic nonsense mutants may be isolated, which allow a vector to be stably maintained in a lactic acid bacterium growing in specific environments including milk, a vegetable material, a meat product, a must, a fruit juice, a wine, a dough, a batter, the gastrointestinal tract, feed crops or offal to be ensiled by a lactic acid bacterium.

The invention is further illustrated in the following non-limiting examples and the drawings wherein FIG. 1 illustrates the construction of vector pFG100. Ligation of a 2.8 kbp EcoRI-BamHI DNA fragment (SEQ ID NO: 25) carrying the replicon of vector pIL2608 and a 298 bp PCR fragment containing supD suppressor allele (SEQ ID NO: 26).

Figure 4:
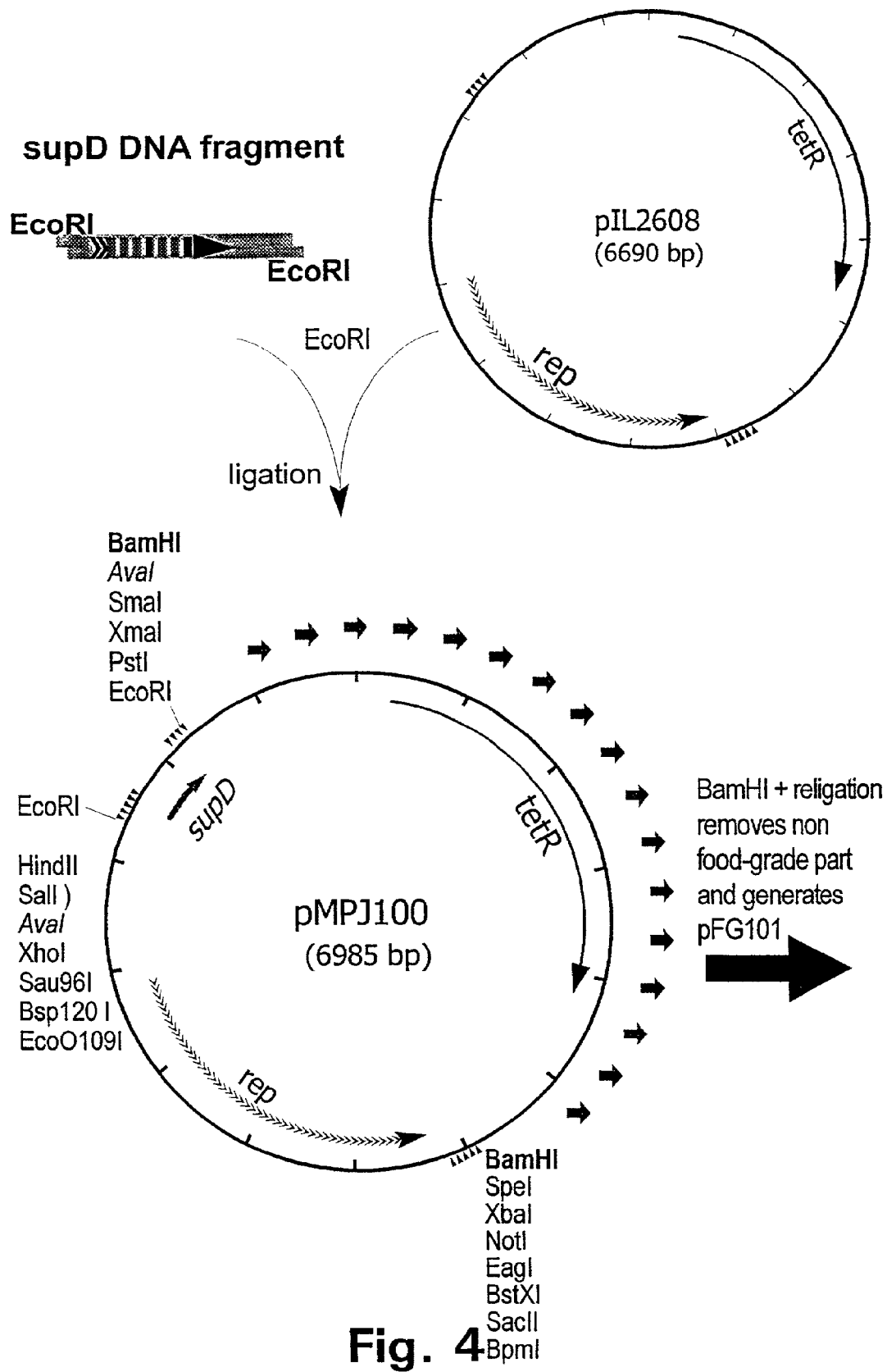
Figure 5:
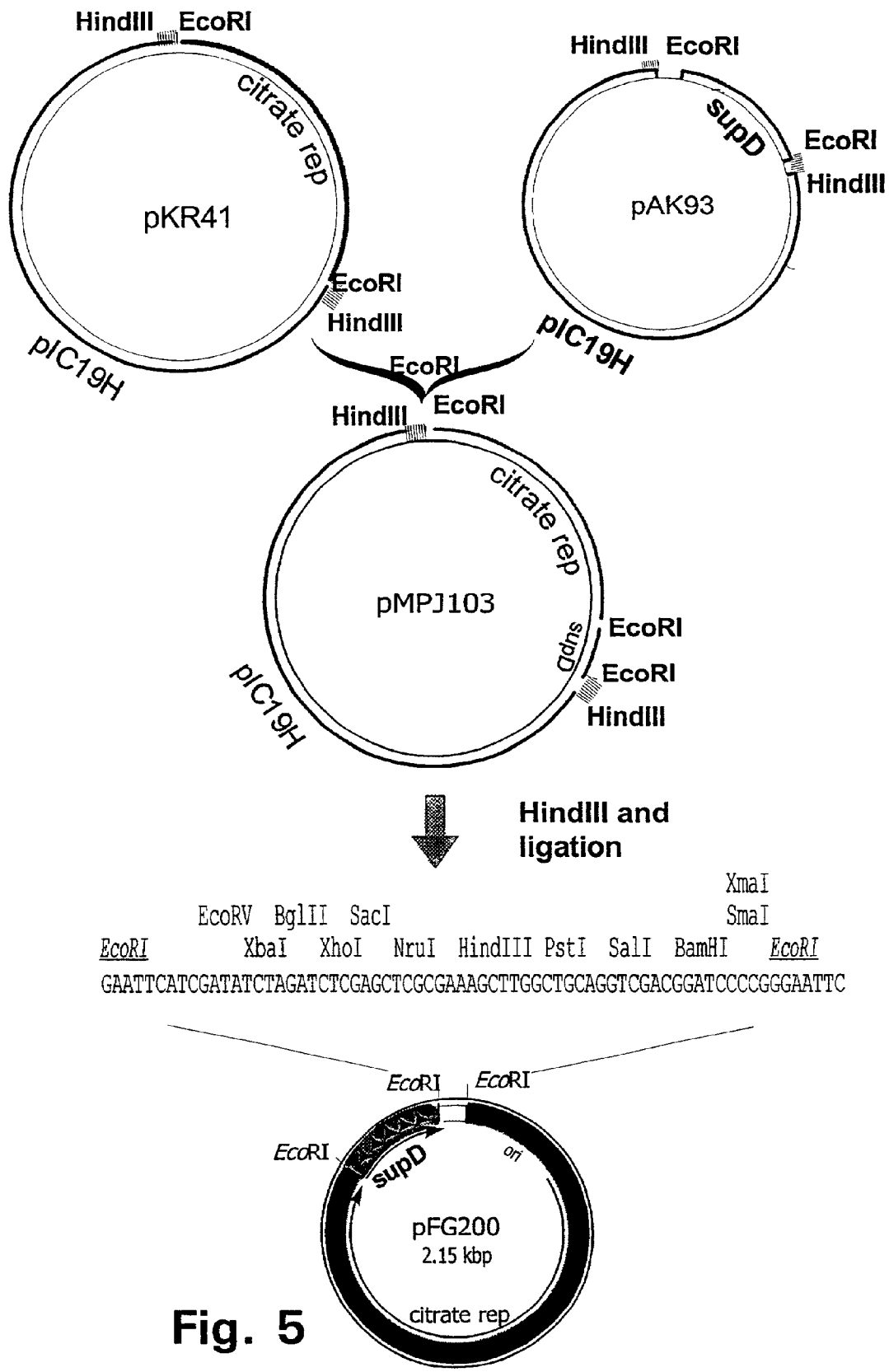

FIG. 4 illustrates the construction of vector pMPJ100. Ligation of a 2.8 kbp EcoRI DNA fragment carrying the replicon of plasmid pIL2608 and a 298 bp PCR fragment containing supD suppressor allele. Filled-in arrows indicate the deletion of the non food-grade part by BamHI digestion of pMPJ100 to generate the food-grade vector pFG100. Only unique cloning sites in pMPJ100 are shown (except BamHI);

FIG. 5 illustrates the construction of vector pFG200. Ligation of an EcoRI digestion of plasmid pKR41 carrying a replicon and an EcoRI digestion of pAK93 carrying the amber suppressor resulting in the plasmid pMPJ103. HindIII-digestion of pMPJ103, self-ligation and electroporation of strain FA4-1-1, resulting in vector pFG200 (SEQ ID NO: 27).

Figure 6:
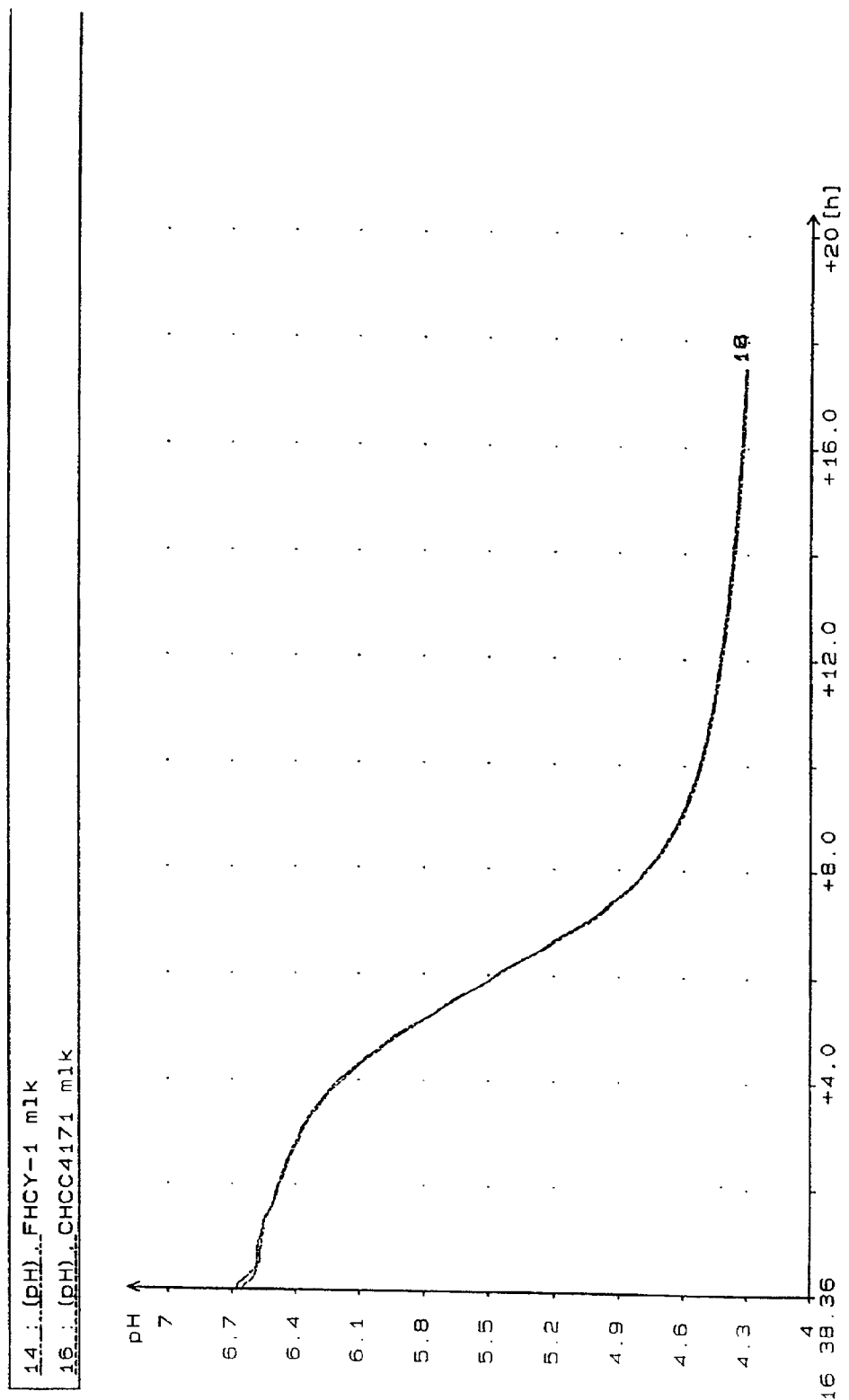
Figure 7:
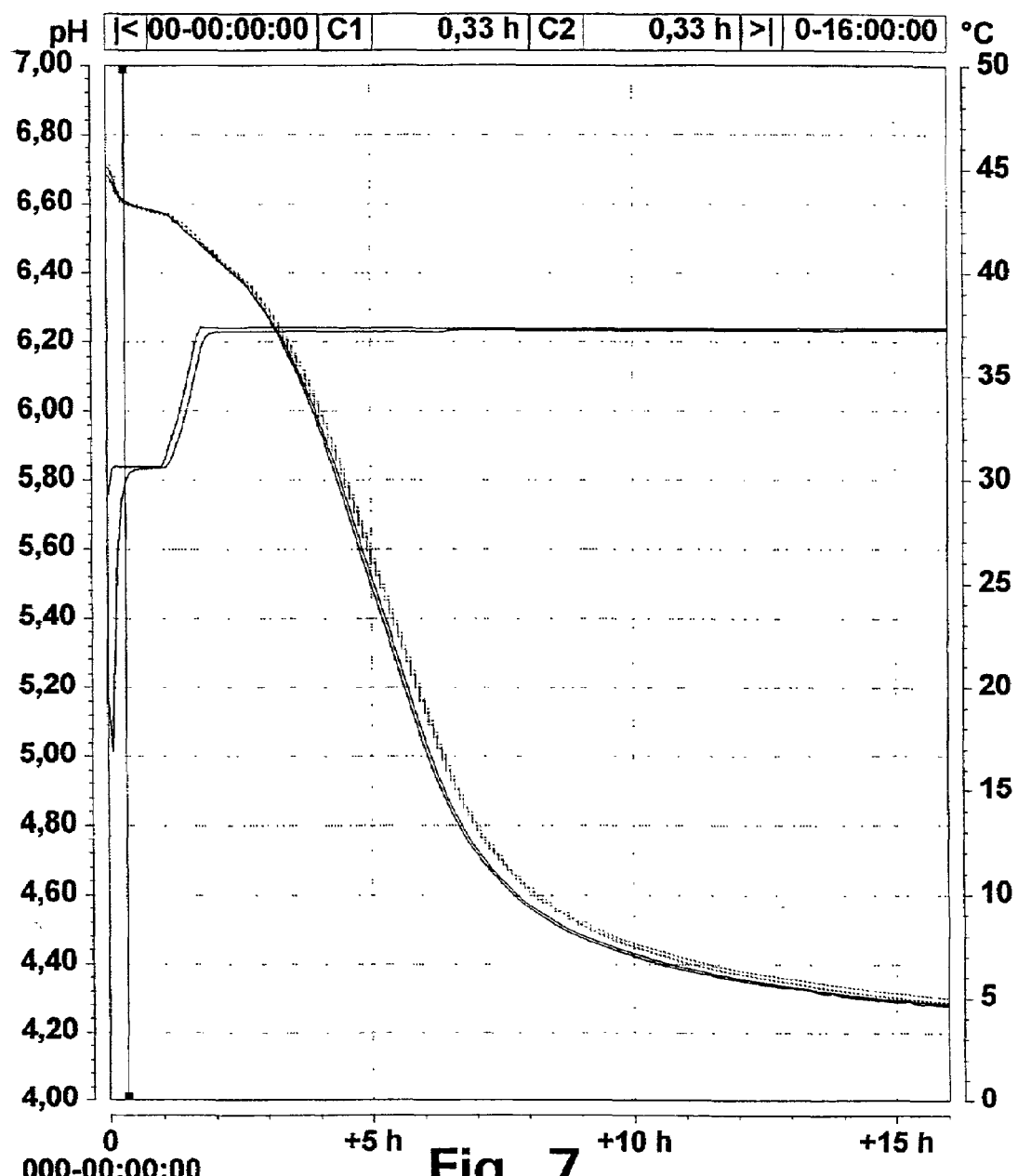
Figure 9:
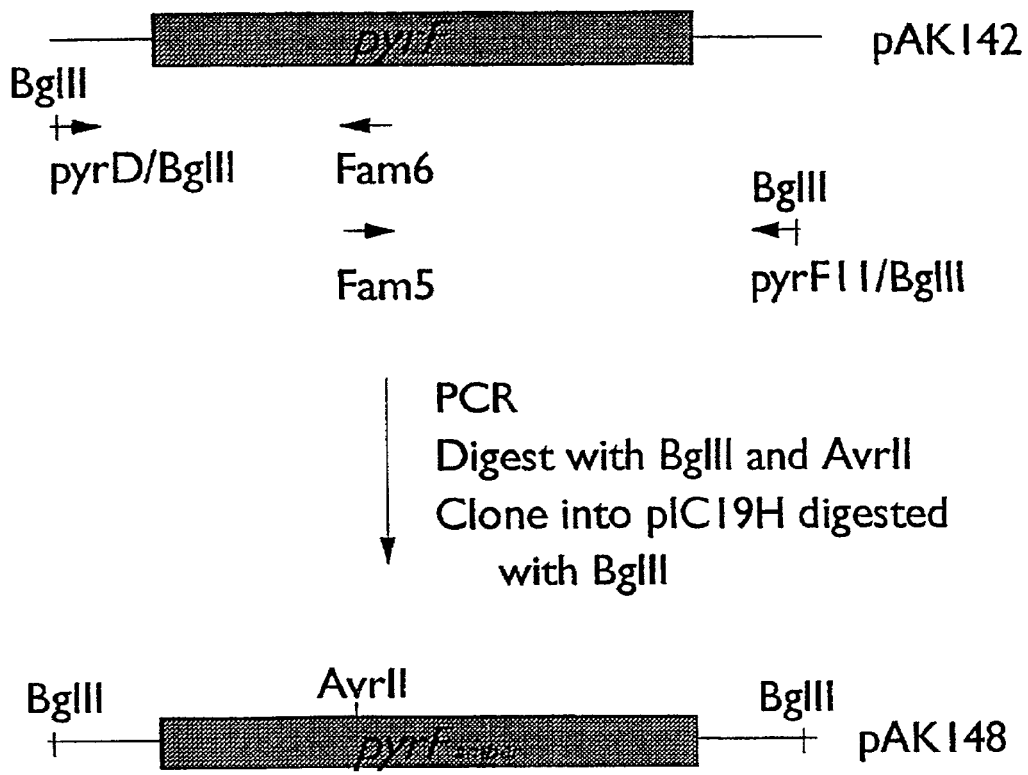

FIG. 6 shows the pH development during 16 hours in whole milk inoculated with strain FH CY-1 or strain CHCC4171 (FH CY-1 pyrF$_{amber}$ containing pFG100);

FIG. 7 shows the pH development during 16 hours in whole milk inoculated with strain FH CY-1 or strain CHCC4223 (FH CY-1 pyrF$_{amber}$ containing pFG200);

FIG. 8 shows the DNA sequence of the pyrF gene of FH CY-1 (SEQ ID NO:23 and SEQ ID NO24);

FIG. 9 illustrates the construction of a pyrF$_{amber}$ mutation; and

Figure 10:
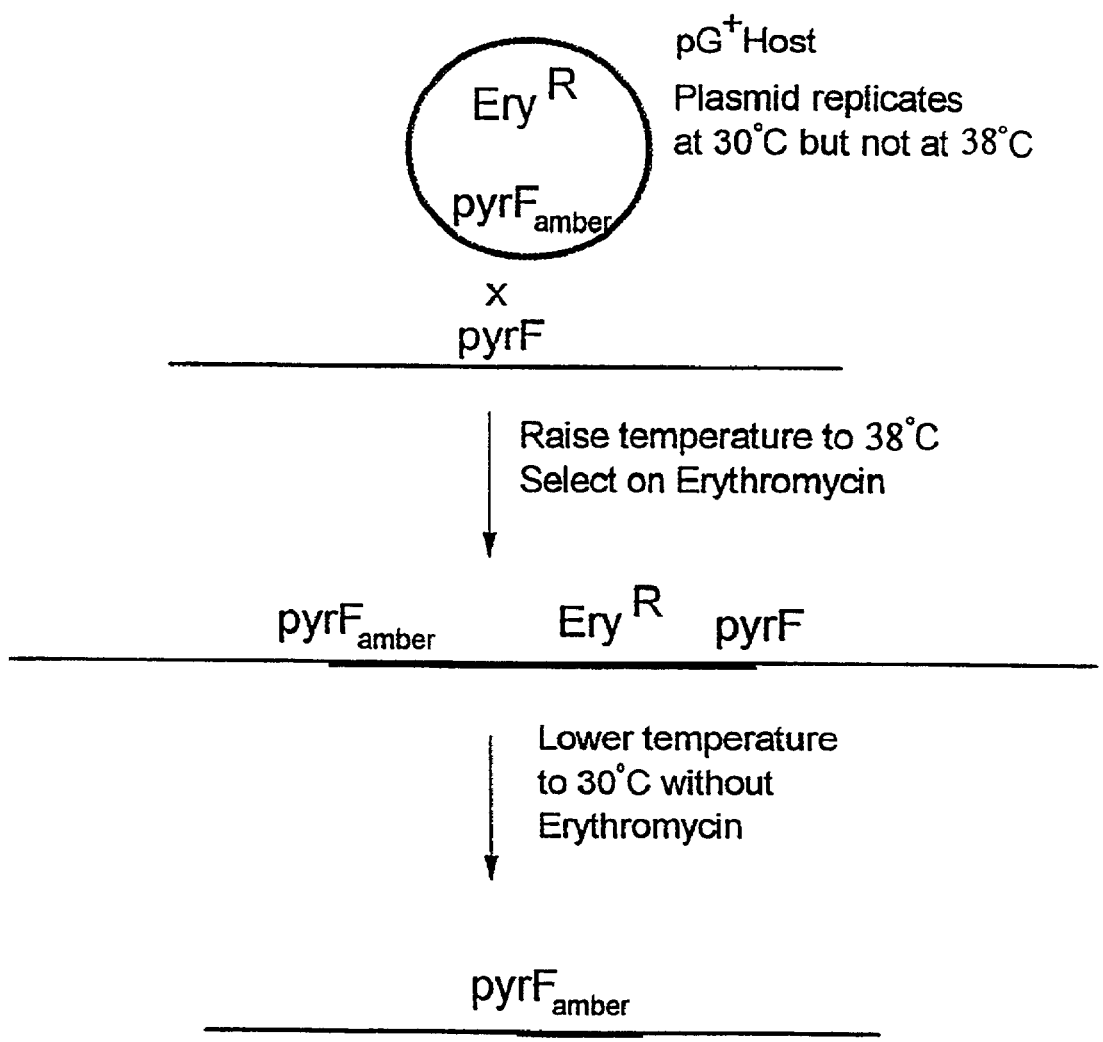

FIG. 10 illustrates the introduction of the pyrF$_{amber}$ mutation into the host strains chromosome.

EXAMPLES

Materials and Methods for the Construction of the Food-Grade Vectors pFG100, pFG101 and pFG200

(i) Bacterial Strains and Plasmids

The following *Lactococcus lactis* strains were used in the examples: strain MG1363 is a plasmid-free derivative of *Lactococcus lactis* strain NCDO 712 (Gasson, 1983). Strain FA4-1-1 deposited on 6 Apr. 1998 under the accession No. DSM 12086 with the Deutsche Sammlung von Mikroorganismen und Zellkulturen GmbH, Mascheroder Weg 1b, D-38124 Braunschweig, Germany having a nonsense mutation that is a pyrimidine auxotroph (pyrF) of strain MG1363, suppressible by an amber suppressor. Strain CHCC4146 deposited on 17 Apr. 1998 under the accession No. DSM 12109 with the Deutsche Sammlung von Mikroorganismen und Zellkulturen GmbH, Mascheroder Weg 1b, D-38124 Braunschweig, Germany is a pyrimidine auxotroph (pyrF) of strain FH CY-1 having a nonsense mutation that is suppressible by an amber suppressor.

The following plasmids were used as sources for replicons: *Lactococcus lactis* plasmid pIL2608 (INRA, France), and *Lactococcus lactis* subsp. *lactis* biovar. diacetylactis citrate plasmid pCT1138.

(ii) Growth Media and Conditions

When strain MG1363 was grown in liquid medium, M17 with 0.5% glucose (GM17) was used. Strain FA4-1-1 or other pyrF-derivatives were cultivated in GM17 medium or DN minimal medium (Dickely et. al. 1995) with 40 µg/ml uracil and/or 40 µg/ml thymidine added. Solid medium (agar plates) was made by the addition of 1.5% agar to the liquid medium. Selection and maintenance of vectors carrying the supD allele in pyrF⁻ strains were performed in minimal medium without pyrimidine sources. Selection of plasmid pMPJ100 was also carried out in media containing 10 g tetracycline. The growth temperature was 30° C. Exponential growth on minimal medium was measured by monitoring the increase in OD at 600 nm.

(iii) Preparation of Competent Cells

Competent cells of strain MG1363 and derivatives were prepared by growing the cells in rich medium containing 1% glycine and for FH CY-1 derivatives 1.5% glysin (Holo and Nes, 1989). Pyrimidine requiring strains were grown in medium containing 40 µg/ml uracil and/or 40 µg/ml thymidine to reduce the frequency of revertants. Cells were harvested at an $OD_{600}$ of 0.6-0.8, resuspended in 0.5M sucrose/10% glycerol and then frozen at −80° C.

(iv) Electroporation of Glycine-Grown Competent Cells

The conditions for electroporation were in all experiments: 25 µF, 200 W, 2.0 kV. Using these conditions with desalted DNA, the typical time constant was 4.8 (Holo and Nes, 1989).

(v) Plasmid Purification

Purification of plasmids from lactococcal strains was carried out as described by Pedersen et al. 1994. Larger preparations of plasmid DNA were prepared using a plasmid purification kit as described by the supplier (QIAGEN®, Stratagene®, Genomed®) by including an initial step of lysozyme treatment. Plasmid DNA preparations were kept at 4° C. in 10 mM Tris (pH 7.5).

(vi) PCR-Reactions

PCR-amplification of the supD gene was performed using 50 ng of pAK89 as template, 10-50 pmol of each primer, 0.25 mM of dNTP, 0.5 units of Taq enzyme in diluted (1×) buffer, which is supplied with the enzyme. The total volume was 50 µl. The reaction conditions were: 94° C. for 4 min, 35 cycles of 94° C., 1 min; 50° C., 1 min, 72° C.; finally 72° C. for 7 min.

(vii) Agarose Gel Electrophoresis

Agarose gel electrophoresis was used for verification of purified DNA, digested DNA, ligated DNA or for further purification of separated DNA fragments. To separate DNA fragments above 500 bp, DNA was loaded and electrophoresed through an agarose gel made with 1% agarose in a Tris-Borate, EDTA buffer. To test and separate DNA fragments less than 500 bp in size, a gel with a higher agarose content was used (1.5-2%). The electrophoresis was performed by applying 100V for 45-60 minutes using a Biorad Power supply Model 200, 2.0.

Example 1

The Construction of the Food-Grade Vector pFG100

1.1 Introduction

In order to use genetically manipulated microorganisms in food products, vectors that are derived totally from the organism to be manipulated are desirable. A useful vector contains a replication region, a selectable marker and a multiple cloning site allowing insertion of desirable genes. In addition, it should be small enough to allow insertion of desired DNA without difficulty.

A multi-copy food-grade cloning vector, pFG100 replicating in lactic acid bacteria was constructed which is based totally on DNA sequences from *Lactococcus*. pFG100 contains the replication region of the *Lactococcus lactis* plasmid pIL2608, an amber suppressor encoding gene, supD, and a multiple cloning site (SEQ ID NO:25 and SEQ ID NO:26). The plasmid is present in >5 copies per cell and exhibits a stable phenotype in various Lactococcal strains.

1.2 Construction of pFG100 by Combining the Replication Region with the Suppressor Gene Vector pFG100 was constructed by ligation of a 2.8 kbp EcoRI-BamHI DNA fragment carrying the replicon of the plasmid pIL2608 to a 298 bp PCR fragment containing the supD suppressor allele. This PCR fragment was generated with plasmid pAK89 (Dickely et al. 1995) as template by using the following primers:

amber-3 (SEQ ID NO:2): (CGAATTCATATTTGATTAAT-GAGAATATGGAACC)

amber-4 (SEQ ID NO:3): (CGGGATCCTTTCAGGAAGG-TAATTAAC)

Figure 1:
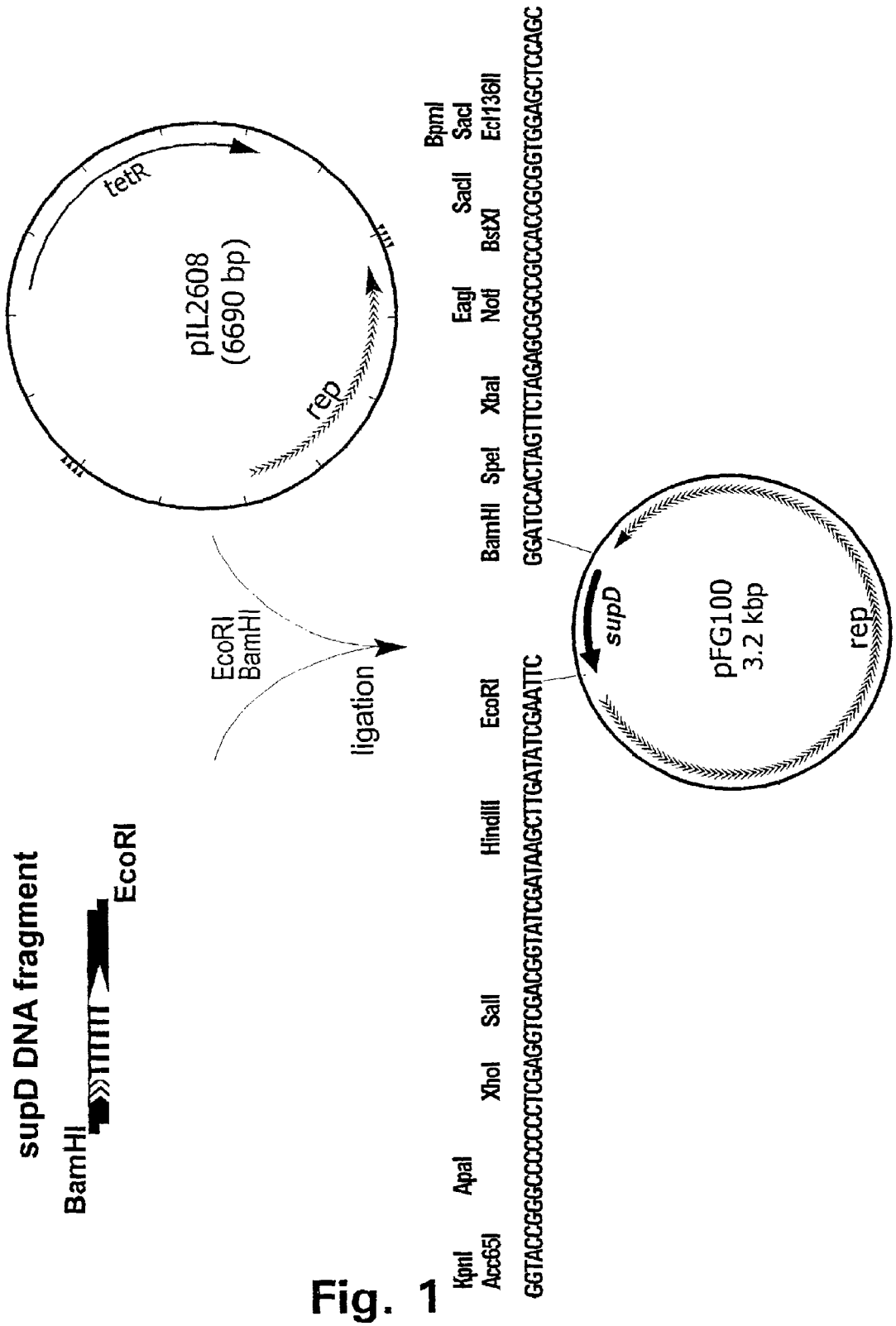

The primers are complementary to the promoter region and downstream region of supD (FIG. 1). The primers were carrying EcoRI and BamHI linkers respectively, which after digestion gave ends compatible for ligation to the replicon fragment of pIL2608.

1.3 Selection of pFG100

As the primary bacterial host strain for the ligated DNA, strain MG1363 was chosen as this strain can be made more competent than the pyrF strain FA4-1-1.

Since strain MG1363 does not carry a stop-codon in the pyrF gene, this strain cannot be used for direct selection of pFG100. In order to select for pFG100, strain MG1363 was co-transformed with pFDi3 (Dickely et. al. 1995), which carries an amber stop-codon in the gene coding for erythromycin resistance. Using this approach a total of 18 colonies were obtained on GM17 agar plates containing 1 µg/ml erythromycin. No colonies appeared on the control plate (MG1363/pIL2608+pFDi3). Eight of the colonies were streaked to single colonies for purification and after plasmid preparation, one clone harbouring pFDi3 and pFG100 was selected. After agarose gel electrophoresis, vector pFG100 was cut out from the gel.

1.4 Transformation of the Bacterial Strain FA4-1-1

The isolated pFG100 vector was introduced into FA4-1-1 by electroporation of glycine-grown competent cells to transform FA4-1-1 to pyrimidine prototrophy. The strain FA4-1-1 containing the vector pFG100 was deposited on 6 Apr. 1998 under the accession No. DSM 12091 with the Deutsche Sammlung von Mikroorganismen und Zellkulturen GmbH, Mascheroder Weg 1b, D-38124 Braunschweig, Germany.

The electroporation efficiency with pFG100 into FA4-1-1 is highly variable. To obtain good competent cells of FA4-1-1, it is recommended that the strain is grown exponentially in the presence of a pyrimidine source as described above. The OD at 600 nm should not exceed 0.7. Using these conditions, good competent cells were obtained regularly. The typical electroporation efficiency with pFG100 DNA has been calculated to $1-5 \times 10^5$ colonies per µg DNA. For direct electroporation of small amounts of ligated DNA, FA4-1-1 was found to be unsuitable as host.

1.5 Growth and Stability of Bacterial Strains Harbouring pFG100 pFG100 can be transformed into the bacterial host strain FA4-1-1 with relatively good efficiency and then isolated with reproducible result. Plasmid isolations from FA4-1-1 tend to yield chromosomal DNA to a higher level than usual.

Figure 2:
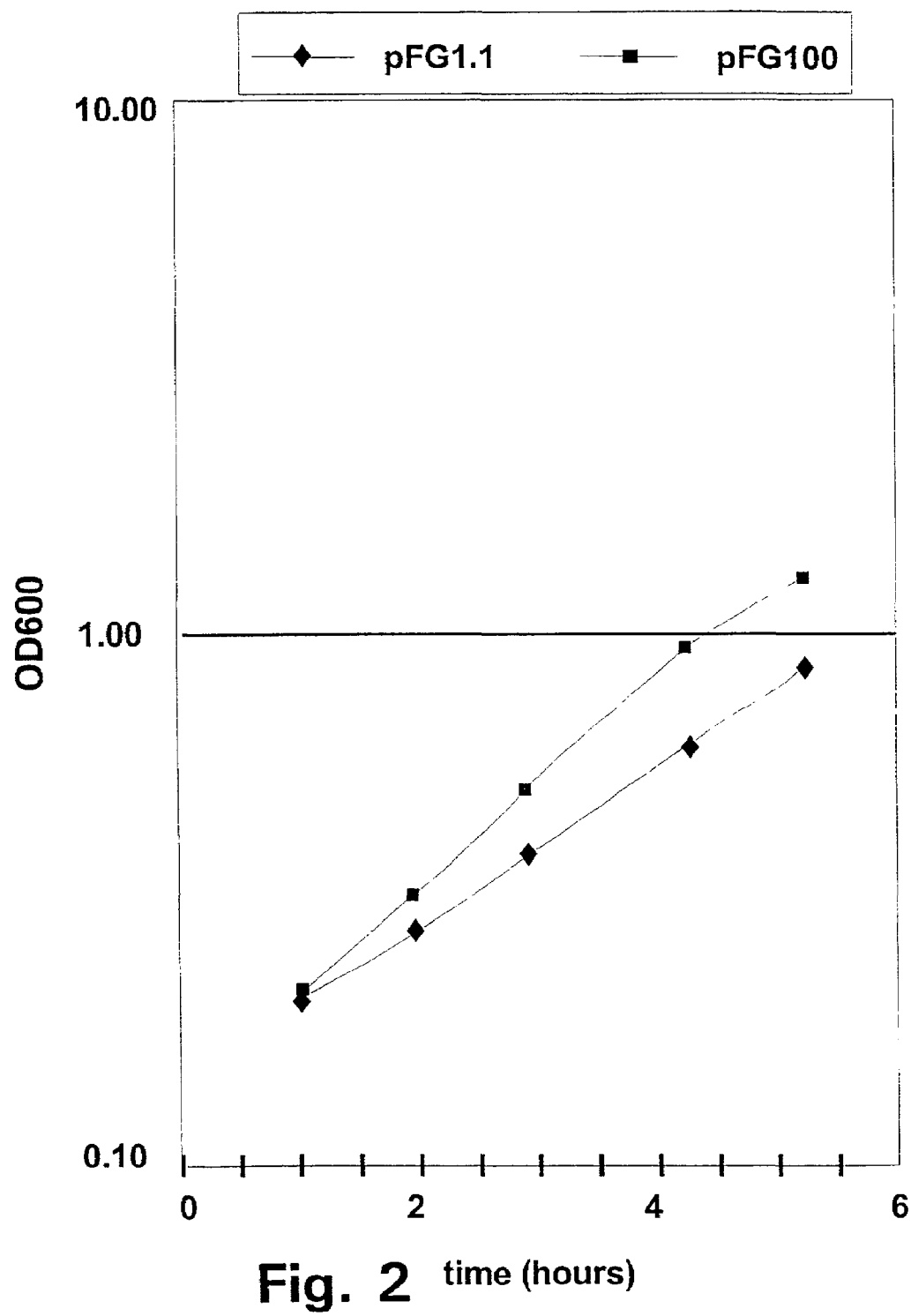
FIG. 2 shows the growth rate of strain FA4-1-1 harbouring pFG100 compared to the growth rate of strain DN209 harbouring pFG1.1.

The growth rate of FA4-1-1 harbouring pFG100 has been measured and compared to the growth rate of DN209/pFG1.1 deposited on 6 Apr. 1998 under the accession No. DSM 12088 with the Deutsche Sammlung von Mikroorganismen und Zellkulturen GmbH, Mascheroder Weg 1b, D-38124 Braunschweig, Germany (Table 1 and FIG. 2). Vector pFG1.1 is a pFG1 derivative (Dickely et. al. 1995) with a mutation in the supB promoter, which reduces supB expression and allows the host strain to grow faster.

TABLE 1

Growth rate of strain FA4-1-1 harbouring pFG100 compared to the growth rate of strain DN209 harbouring pFG1.1. on minimal medium

| Time | pFG1.1 | pFG100 |
|---|---|---|
| 12:01 | 0.20 | 0.21 |
| 12:50 | 0.27 | 0.30 |
| 13:48 | 0.37 | 0.57 |
| 15:05 | 0.61 | 1.04 |
| 16:00 | 0.84 | 1.41 |

FA4-1-1/pFG100 was found to grow with a doubling rate of 86 minutes which is 19 min faster than DN209/pFG1.1 (105 minutes) (FIG. 2).

Figure 3:
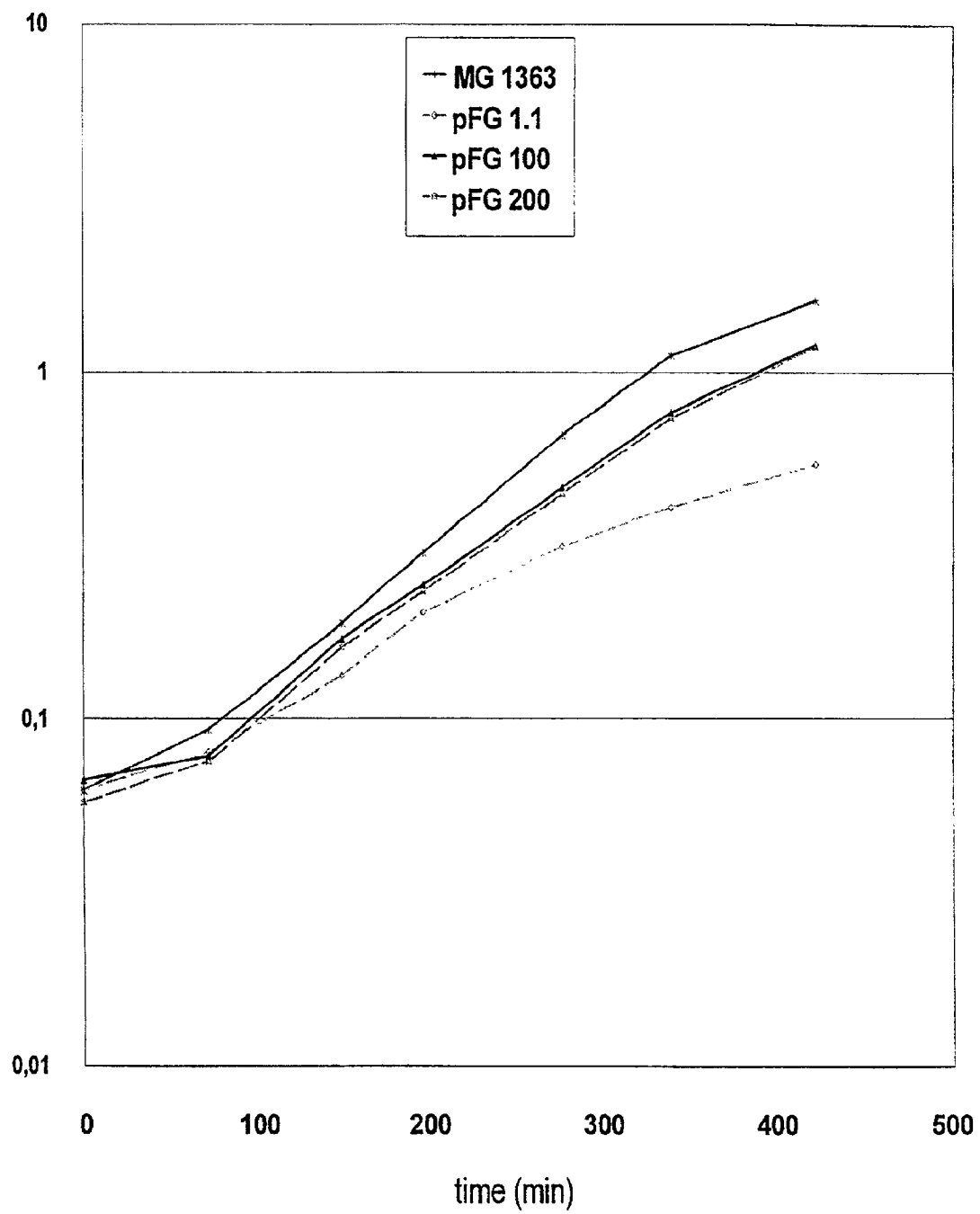
FIG. 3 shows the growth rates of the mother strain MG1363, DN209 harbouring pFG1.1, FA 4-1-1 harbouring pFG100 and FA 4-1-1 harbouring pFG200 (each determined twice)

In a comparative study of the growth rates of the parental strain MG1363, strain DN209/pFG1.1, strain FA 4-1-1/pFG100 and strain FA 4-1-1/pFG200 (Table 2, FIG. 3), the strains were found to grow with a doubling rate of 66 min, 115 min, 77 min and 77 min, respectively.

TABLE 2

Growth rates of strain MG1363, strain DN209/pFG1.1, strain FA 4-1-1/pFG100 and strain FA 4-1-1/pFG200 on minimal medium

| Time (min) | MG1363 | pFG1.1 | pFG100 | pFG200 |
|---|---|---|---|---|
| 0 | 0.063 | 0.063 | 0.067 | 0.058 |
| 71 | 0.094 | 0.081 | 0.079 | 0.076 |
| 149 | 0.190 | 0.134 | 0.172 | 0.162 |
| 196 | 0.304 | 0.204 | 0.245 | 0.235 |
| 276 | 0.660 | 0.318 | 0.467 | 0.451 |
| 339 | 1.117 | 0.410 | 0.770 | 0.737 |
| 423 | 1.615 | 0.544 | 1.200 | 1.182 |
|  | Td = 66 min | Td = 115 min | Td = 77 min | Td = 77 min |

1.6 Stability of pFG100 in Industrial Production Strains

To test the stability of pFG100 in production strains, the vector was transformed into the pyrF-derivative of strain FH CY-1, strain CHCC4146 to produce strain CHCC4171 which was deposited on 6 Apr. 1998 under the accession No. DSM 12090 with the Deutsche Sammlung von Mikroorganismen und Zellkulturen GmbH, Mascheroder Weg 1b, D-38124 Braunschweig, Germany. The vector was found to be maintained and co-exist with the plasmids of that strain. Importantly, it was also found that growth and lactic acid production was virtually unaffected by the presence of the vector (see Example 4).

1.7 Plasmid Copy Number of pFG100

The copy number of pFG100 was determined by visual comparison by agarose gel electrophoresis with the vector pFG1 which was deposited on 6 May 1994 under the accession No. DSM 9190 with the Deutsche Sammlung von Mikroorganismen und Zellkulturen GmbH, Mascheroder Weg 1b, D-38124 Braunschweig, Germany. These data indicate that pFG100 is present in 5-8 copies per cell corresponding to the copy number of vector pFG1.

Example 2

The Construction of the Non-Food Grade Vector pMJP100 as an Intermediate to Obtain the Food-Grade Vector pFG101

2.1 Introduction

The primary host strain FA4-1-1 exhibits a quite high reversion rate and is difficult to make competent enough for electroporation with ligation mixtures i.e. initial screenings of clones. To circumvent this problem, the pMPJ100 vector was constructed. Like pFG100, this vector is also based on the pIL2608 replicon but in addition to the supD gene, the tet gene is present on the plasmid. This means that the cloning of relevant genes can be screened in MG1363 by selecting for tetracycline resistance. Conversion to food-grade status can then be carried out by a BamHI digestion, ligation and transformation into the final pyrF amber host.

2.2 Construction of Plasmid pMPJ100 by Combining the Replicon Region with the Suppressor Gene Plasmid pMPJ100 was constructed by digestion of plasmid pIL2608 with EcoRI and the DNA with a PCR fragment carrying the supD allele (FIG. 4). This PCR fragment was generated with the plasmid pAK89 (Dickely et. al. 1995) as described in Example 1, but instead of using primer amber-4 (SEQ ID NO:3), the following primer was used to obtain EcoRI compatible sites in both ends of the fragment:

primer amber-6 (SEQ ID NO: 5) (GGGAATTCAGGAAG-GTAATTAACTATGG)

2.3 Transformation of the Bacterial Strain MG1363 with pMJP100

The ligation mixture was introduced into MG1363 by electroporation. Ejectroporation with ½ of the ligation mixture into MG1363 resulted in more than 300 colonies on GM17 agar plates containing 10 tetracycline. Ten colonies from this plate were further purified and used for isolation of plasmid DNA. Two of the 10 colonies were found to contain the supD allele cloned in the same orientation (FIG. 4).

The electroporation efficiency with pMPJ100 DNA is typically the same as with pFG100, as described in Example 1. The electroporation efficiency has been calculated to $1\text{-}5 \times 10^5$ colonies per µg DNA.

2.4 Deletion of the Nonfood-Grade Components of pMJP100 to Obtain the Food-Grade Vector pFG101

Food-grade vector pFG101 can be derived directly from pMPJ100 by BamHI digestion, ligation and transformation into a pyrF-$_{amber}$ host strain (FIG. 4).

Example 3

Construction of the Food-Grade Expression Vector pFG200

The complete minimal replicon of the *L. lactis* subsp. *lactis* biovar diacetylactis citrate plasmid pCT1138 has been cloned as a 1.7 kb polymerase chain reaction (PCR) fragment flanked by EcoRI sites (Pedersen et al., 1994). This fragment contains the origin of replication, the repB gene and ~300 bp of flanking DNA and was cloned in pIC19H (ampicillin resistant, Amp$^R$) to produce pKR41.

PCR was performed on pAK89 using the following primers:

amber-2 (SEQ ID NO:4): (CGAATTCAACATTTTTG-TATAAATATGCG)

amber-3 (SEQ ID NO:2): (CGAATTCATATTTGATTAAT-GAGAATATGGAACC)

The primers were used to produce a PCR fragment containing the tRNA promoter, the suppressor gene and downstream sequences flanked by the EcoRI sites provided by the primers (FIG. 5). This 360 bp EcoRI fragment was cloned in pIC19H to give pAK93.

The supD allele is a suitable selectable marker when combined with the pyrimidine auxotroph FA4-1-1. This strain only grows in pyrimidine-free medium in the presence of the amber suppressor. DNA of pAK93 and pKR41 was digested with EcoRI, mixed, ligated and electroporated into FA4-1-1 followed by selecting prototrophs. This selection ensures that colonies contain plasmids with the suppressor gene and the citrate plasmid replicon. Some plasmids will also contain pIC19H. These were obtained by pooling several hundred colonies, extracting plasmid DNA and transforming *E. coli* selecting Amp$^R$. One plasmid with the desired structure was designated pMPJ103.

All pIC19H except the polylinker was deleted by digesting pMPJ103 with HindIII, self ligating, and electroporating FA4-1-1 selecting prototrophs. Among 300 colonies obtained in total, 20 were selected and tested for plasmid content. More than 50% of these was found to contain a single plasmid of 2.2 kb containing the citrate plasmid replicon, the amber suppressor and the polylinker. One was saved and the plasmid designated pFG200. The vector pFG200 was transformed into the pyrF-derivative of strain FH CY-1, strain CHCC4146 to produce strain CHCC4223 which was deposited on 16 Apr. 1998 under the accession No. DSM 12108 with the Deutsche Sammlung von Mikroorganismen und Zellkulturen GmbH, Mascheroder Weg 1b, D-38124 Braunschweig, Germany. The structure of pFG200 is illustrated in FIG. 5. The resulting polylinker (SEQ ID NO:27) is identical to that found in pIC19R (Marsh et al., 1984) and contains the following unique sites: SmaI, BamHI, SalI, PstI, HindIII, NruI, XhoI, SacI, BglI, XbaI and EcoRV.

Example 4

Construction of pyrF$_{amber}$ Mutants of the Industrial Strain *Lactococcus lactis* FH CY-1

4.1 Introduction

In order to use the previously described food-grade expression vectors based on a supD suppressor capable of suppressing amber mutations, appropriate mutations in a number of industrial *Lactococcus* strains are needed. Rather than use chemical mutagenesis with its inherent problems, single precise alteration in the chromosome of the strains to be used as host for pFG100 or pFG200 were carried out. The pyrF gene was chosen because it exists in a single copy in the *Lactococcus* chromosome, the DNA sequence is known from MG1363, mutants should have an absolute requirement for pyrimidines for growth, and milk does not contain enough pyrimidines to allow growth of the mutants. Thus, milk would be a selective medium for this plasmid.

The DNA sequence of the pyrF gene of FH CY-1 was determined, the pyrF genes was cloned and amber mutations introduced by polymerase chain reaction. Finally, gene replacement was used to introduce the constructed amber mutation into the chromosome of FH CY-1.

4.2 Materials and Methods (i) Growth Media and Strains

*Lactococcus lactis* was grown in M17 or DN minimal medium (Dickely et al., 1995). *Escherichia coli* was grown in LB-media, supplemented with ampicillin to 50 mg/ml when required. For growth of pyr$^-$ strains, uracil was added to 20 mg/ml. Competent cells of FH CY-1 were made by growth in the presence of 1.5% glycine (Holo and Nes, 1989).

Strain FH CY-1, which was deposited on 6 Apr. 1998 under the accession No. DSM 12087 with the Deutsche Sammlung von Mikroorganismen und Zellkulturen GmbH, Mascheroder Weg 1b, D-38124 Braunschweig, Germany, is the industrial strain of *Lactococcus lactis* also known as CHCC377 and is the major component of the R604 culture. *Escherichia coli* strain DH5α was used for cloning in pIC19H.

(ii) DNA Preparation and Manipulations

Plasmid preparations from *Escherichia coli* was prepared by using a plasmid purification kit as described by the supplier (QIAGEN®, Stratagene®), Genomed®) by including an initial step of lysozyme treatment. Plasmid DNA was isolated from *Lactococcus lactis* by using the procedure of Pedersen et al. (1994) with the modification that 50 ml of 5M NaCl was added before the phenol extraction. Chromosomal DNA was purified from *Lactococcus lactis* by using the procedure of Johansen and Kibenich (1992).

Digestion with restriction enzymes, ligations and polymerase chain reactions were made by following the procedure of the manufacturers of the various enzymes and kits. DNA sequencing was by cycle sequencing as recommended by Perkin-Elmer. The resulting products were purified on BioRad Micro-Bio-Spin-Chromatography columns before running on the ABI310 DNA sequencer. The primers used are shown in Table 3.

TABLE 3

| Primer used | | |
|---|---|---|
| pyrF1 | SEQ ID NO:6 | GCAGATCTAAGCTTGATTCAAGAAGTAAAAGAAGGC |
| pyrF2 | SEQ ID NO:7 | ATAGATCTACTCGATGCCAAGAATGGACCGC |
| pyrF3 | SEQ ID NO:8 | AAAGGCCTGTNATNGCNCTNGAYTTYCC |
| pyrF4 | SEQ ID NO:9 | TGGACGAATTCCNGGNGT |
| pyrF5 | SEQ ID NO:10 | CATAGTAAACGACTTGGGG |
| pyrF6 | SEQ ID NO:11 | TACGCACAAAAAACCGCT |
| pyrF7 | SEQ ID NO:12 | GGTCGCCTTTACTTGCACC |
| pyrF8 | SEQ ID NO:13 | GATTATATTGTTGTCGGCCG |
| pyrD-degn | SEQ ID NO:14 | GCTCTAGAGCMWATYGWWATDGGN |
| IlagidB2 | SEQ ID NO:15 | GGTNGARTGGAAYGARAARATHAAY |
| Fam5 | SEQ ID NO:16 | CCTCAACCTAGGAGAAAATTATGC |
| Fam6 | SEQ ID NO:17 | TCTCCTAGGTTGAGGTTAATTGTG |
| pyrD/BglII | SEQ ID NO:18 | ATAGATCTGCTTAGAAAACTTG |
| pyrF11/BglII | SEQ ID NO:19 | ATAGATCTGCATGTAAGCAAAAACC |

(iii) Plasmid Stability in Milk

A fresh overnight culture of CHCC4171 (DSM 12090) and CHCC4223 (DSM 12108) in minimal medium was subcultured 1:100 (100 µL into 10 ml) in reconstituted skim milk (RSM) and incubated overnight. The resulting culture was plated on M17 plates and subcultured 1:100 in RSM. This procedure was repeated for five consecutive days. Each outgrowth was taken to be 7 generations ($2^7$=128). After each outgrowth, 100 single colonies were picked and patched onto minimal and minimal+uracil plates. A strain which has lost the pFG100 or pFG200 plasmid will be unable to grow on minimal plates but will grow on minimal+uracil plates. A strain retaining the plasmid will grow on both plates. To confirm this, plasmids were isolated from 10 colonies after 35 generations. All had the expected plasmid profile.

(v) Acidification Studies in Whole Milk

Single colonies of strain FH CY-1 (DSM 12087), and CHCC4171 (FH CY-1 pyrF$_{amber}$/pFG100), DSM 12090) were inoculated in M-17 or DM-9,5-UA media. The cultures were incubated for 24 hours at 30° C. Subsequently, the cultures (1%) were inoculated in whole milk and incubated in a warm water-bath (Profilur) equipped with a pH-electrode (Hammilton). The pH development was registered continuously for 16 hours (FIG. 6). In addition, comparative acidification studies with strain FH CY-1 and CHCC4223 (FH CY-1 pyrF$_{amber}$/pFG200), DSM 12108) were performed in accordance with the method as described above (FIG. 7).

4.3 Sequencing of the pyrF Gene of Strain FH CY-1

The DNA sequence of the pyrF gene of MG1363 is known (Andersen et al., 1994). Primers based on this sequence (pyrF1 and pyrF2, Tab. 3) were tested but could not be used to clone or sequence the pyrF gene of FH CY-1. Based on an amino acid sequence comparison of the pyrF gene product of a number of microorganisms, two degenerate primers (pyrF3 and pyrF4, Tab.3) were made and used to amplify a 550 bp internal pyrF fragment. This fragment was sequenced with the same primers. Based on this sequence, new primers were ordered (pyrF5 and pyrF6, Tab. 3) and used for inverse PCR with Sau3Al digested DNA. This gave additional sequence data. The sequence of the amino terminal end of pyrF was completed using a degenerate primer designed from the sequence of pyrD (pyrD-dgen, Tab. 3) which is immediately upstream of pyrF and two additional primers (pyrF7 and pyrF8, Tab. 3). The carboxy terminal end of pyrF was sequenced using a degenerate primer (llagidB2, Tab. 3) designed from the sequence of gidB, which is immediately downstream of pyrF, and pyrF6. The DNA sequence of the pyrF gene of FH CY-1 is presented in FIG. 8. This gene is 86% identical to the pyrF gene of MG1363.

4.4 Cloning of the pyrF Gene of Strain FH CY-1

Primers for PCR amplification were designed from the DNA sequences determined above (pyrD/BglII and pyrF11/BglII). They contain BglII restriction sites and allow amplification of a ca. 1.1 kb DNA fragment containing the entire pyrF gene. This fragment was cloned into pIC19H digested with BglII. The pyrF gene of strain FH CY-1 is contained in a plasmid designated pAK142.

4.5 Introduction of an Amber Mutation into the Cloned pyrF Genes

The strategy used involves searching the DNA sequence for a serine codon (TCT, TCC, TCA, TCG, AGT or AGC) that can be changed to amber (TAG) and which is flanked by sequences that allow the introduction of a restriction enzyme recognition site without affecting the amino acids encoded by the flanking sequences. This is illustrated below:

```
Fam5 (SEQ ID NO:16)              5' CC TCA ACC TAG GAG AAA ATT ATG C 3' ->
                                    || ||| ||* |** ||| ||| ||| ||| |
       5' ...              ACA CAA TTA ACC TCA ACT TCT GAG AAA ATT ATG CAA ... 3'

3' ...              TGT GTT AAT TGG AGT TGA AGA CTC TTT TAA TAC GTT ... 5'
                                    | ||| ||| ||| ||| ||* |** ||| |
Fam6 (portion of SEQ ID NO:16)<-3' T GTT AAT TGG AGT TGG ATC CTC T 5'
```

The PCR primers are called Fam5 and Fam6 (Tab. 3) and are indicated above and below the sequence of this region of pyrF (SEQ ID NO:20 and SEQ ID NO:21). The mismatched base pairs are indicated by *. The outside primers are pyrF11/BglII and pyrD/BglII (Tab. 3) to facilitate cloning of the resulting PCR products. Following PCR and cloning as described in FIG. 9, the DNA sequence (SEQ ID NO:22) will be:

```
                                          amber
5' . . . ACA CAA TTA ACC TCA ACC TAG GAG AAA ATT ATG CAA . . . 3'
         T   Q   L   T   S   T   α
```

(SEQ ID NO: 28) where the amber codon is indicated by ▯ and the introduced AvrII restriction site is underlined. Suppression of this amber mutation by supB will introduce a serine and the amino acid sequence of the resulting protein will be identical to that of the parent strain.

The pyrF$_{amber}$ DNA fragment was cloned in pIC19H to make plasmid pAK148 and the DNA sequence determined. No undesired changes were detected.

4.6 Introduction of the Amber Mutation into the Chromosome

The pyrF$_{amber}$ DNA fragment was subcloned into pG$^+$Host9 to produce plasmid pAK149. The pG$^+$ Host vectors are temperature sensitive for replication and can be used to integrate DNA into the *Lactococcus* chromosome (FIG. 10). These vectors replicate at 30° C. but not at temperatures above 36° C. The strain FH CY-1/pAK149 was constructed by electroporation and is resistant to erythromycin by virtue of the erythromycin-resistance gene present in pG$^+$Host9.

When FH CY-1/pAK149 is incubated at 38.0° C. and plated on M17 Ery plates, surviving colonies will be strains in which pAK149 has integrated into the chromosome by homologous recombination between the pyrF$_{amber}$ fragment on pAK149 and the pyrF gene on the chromosome. The resulting strains have two copies of pyrF, one normal and one mutant. One such strain was purified and saved as FH CY-1/pAK149 Nr 1.

Bacteria cannot survive if they have two active replicons in their chromosome, so incubation of a strain like FH CY-1/pAK149 Nr 1 at 30° C. will select for strains in which the integrated pG$^+$Host derivative has been removed. This can most easily occur by a second homologous recombination event. Depending on where this event occurs, the chromosome will either contain the normal pyrF gene or the pyrF$_{amber}$ gene. Strains in which the desired recombination event has occurred are found by screening survivors isolated on M17 plates at 30° C. for their pyrimidine requirement. Strains that do not require pyrimidines for growth have the normal pyrF gene while strains that require pyrimidines have the pyrF$_{amber}$ gene. This process of integration and excision of pAK149 is illustrated in FIG. 7. The overall result is that the pyrF$_{amber}$ gene originally on the plasmid and indicated by the dark line replaces the pyrF gene originally on the chromosome.

Pyr$^-$ survivors were tested for the presence of the amber mutation by amplifying the pyrF gene via PCR and confirming that the AvrII restriction site was still present. The DNA sequence of the pyrF gene was also determined following PCR amplification. One strain with exactly the desired DNA sequence of the pyrF$_{amber}$ gene was saved and deposited as CHCC4146 (DSM 12109). Thus, the strain CHCC4171 (DSM 12090) may be cured for the vector pFG100 to obtain strain CHCC4146 as described in Dickely et al. 1995 and WO 95/10621.

4.7 Introduction of pFG100 and pFG200 into CHCC4146 and Characterisation of the Resulting Strains, CHCC4171 and CHCC4223

Competent cells were made and electroporation with pFG100 were done. Ten colonies growing on minimal medium were purified and plasmid analysis showed that five of the colonies contained pFG100. The other five were spontaneous pyr$^+$ revertants. One strain was saved and designated CHCC4171 (DSM 12090).

Plasmid stability was tested and 100 of 100 colonies tested at each of 7, 14, 21, 28 and 35 generations in milk were found to contain pFG100. Thus, this plasmid is very stable in the FH CY-1 background. This is a significant improvement over the pFG1 system (WO 95/10621) which had over 90% plasmid-free cells after 40 generations in milk.

The acidification of milk by FH CY-1 and CHCC4171 was assessed as described above. The two strains were virtually indistinguishable and showed the high rate of acidification characteristic for FH CY-1 (FIG. 6). Furthermore, the acidification rate of strain CHCC4223 was as high as that of strain CHCC4171 and virtually indistinguishable from strain FH CY-1. This too was a significant improvement over the pFG1 system where the acidification rate for various FH CY-1 derivatives was considerably reduced.

4.8 Application of the Food-Grade Cloning System

The functionality of the pFG200 was assessed by cloning of the pepN gene of L. lactis strain Wg2, encoding lysine aminopeptidase into the vector. The resulting plasmid, pFG202, was transformed into FA6-3 and CHCC4146 which then were grown in parallel with the host strains without plasmids (chromosomal pepN gene alone). After sonification of the harvested cells, the cell-free extracts were used to determine the PepN activity. The determined activities of lysine aminopeptidase are presented in Table 4 and show significant increases of PepN activity in both the MG1363 background strain (FA 6-3) and in the FHCY-1 background strain (CHCC4223).

TABLE 4

The effect of cloning the pepN gene into pFG200 by presenting the result of pepN overexpression in the MG1363 background strain (FA 6-3) and in the FHCY-1 background strain (CHCC4223).

| Strain | Activity of lysin aminopeptidase[a] |
| --- | --- |
| FA 6-3 | 55 |
| FA 6-3/pFG202 | 339 |
| CHCC4146 | 17 |
| CHCC4146/pFG202 | 211 |

[a]Determined as unit of lysine aminopeptidase per mg of protein

In addition, the lysin gene of the bacteriophage ML3 into pFG200 has been cloned. As expected, transformation of the generated plasmid construct into a host strain resulted in a much faster rate of lysis (no data shown).

REFERENCES

1. Andersen, P. S., Martinussen, J. and Hammer, K. 1996. Sequence analysis and identification of the pyrKDbF operon from *Lactococcus lactis* including a novel gene, pyrK, involved in pyrimidine biosynthesis. Journal of Bacteriology, 178: 5005-5012.
2. Demerec, M., E. A. Adelberg, A. J. Clark and P. E. Hartman 1966: A proposal for a uniform nomenclature in bacterial genetics. Genetics 54, 61-76.
3. Dickely, F., Nilsson, D., Hansen, E. B. and Johansen, E. 1995. Isolation of *Lactococcus lactis* nonsense suppressors and construction of a food-grade cloning vector. Mol. Microbiol. 15: 839-847.
4. Eggertson, G. and Söll, D. 1988. Transfer ribonucleic acid-mediated suppression of termination codons in *Escherichia coli*. Microbiol. Rev. 52: 354-374.
5. Johansen, E., Dickely, F., Nilsson, D. and Hansen, E. B. 1995. Nonsense suppression in *Lactococcus lactis*: Construction of a "Food-Grade" cloning vector. Dev Biol Stand. Basel, Karger, 1995, vol 85, pp. 531-534.
6. Gasson, M. J. 1983: Plasmid complements of *Streptococcus lactis* NCDO712 and other lactis streptococci after protoplast induced curing. J. Bacteriol. 154, 1-9.
7. Holo, H. and Nes, I. F. 1989. High frequency transformation, by electroporation, of *Lactococcus lactis* subsp. *cremoris* grown in glycine osmotically stabilized media. Appl. Environ. Microbiol. 55: 3119-3123.
8. Johansen, E. and Kibenich, A. 1992. Characterization of *Leuconostoc* isolates from commercial mixed strain mesophilic starter cultures. J. Dairy Sci. 75: 1186-1191.
9. Marsh, J. L., Erfle, M. and Wykes, E. J. 1984. The PIC plasmid and phage vectors with versatile cloning sites for recombinant selection by insertional inactivation. Gene 32: 481-485.
10. Pedersen, M. L., Arnved, K. R., and Johansen, E. 1994. Genetic analysis of the minimal replicon of the *Lactococcus lactis* subsp. *lactis* biovar. diacetylactis citrate plasmid. Mol Gen Genet 244: 347-382.

The invention claimed is:

1. A recombinant vector that is selected from a group consisting of pFG100 deposited under the accession No. DSM 12091, and pFG200 deposited under the accession No. DSM 12108.

2. A lactic acid bacterium that is *Lactococcus lactis* subsp. *lactis* strain FA4-1-1 containing pFG100, deposited under the accession No. DSM 12091 or *Lactococcus lactis* subsp. *lactis* strain CHCC4146 containing pFG200, deposited under the accession No. DSM 12108.

3. A method for stably maintaining a recombinant vector in lactic acid bacterial host cells, growing in a particular environment, which method comprises:
   (A) providing mutant cells that are auxotrophic lactic acid bacterial cells, which cannot grow in said environment and which carry a nonsense mutation in a pyr gene; and
   (B) producing said host cells by transforming said nonsense mutant cells with a vector that lacks a gene coding for antibiotic resistance and that comprises (i) lactic acid bacterial DNA, (ii) a gene coding for an amber suppressor that is a tRNA comprising the CUA anticodon, and (iii) a replicon that makes said vector capable of replicating in a lactic acid bacterium, such that said host cells do not grow if they lose said vector.

4. A recombinant vector comprising:
   (A) lactic acid bacterial DNA;
   (B) a first gene coding for an amber suppressor that is a tRNA comprising the CUA anticodon;
   (C) a replicon making said vector capable of replicating in a lactic acid bacterium;
   (D) a second gene coding for a desired gene product,
   wherein (a) said vector lacks a gene coding for antibiotic resistance, (b) said gene product is a bacteriophage lysin, and (c) said second gene is obtained from the bacteriophage ØvML3 as contained in DN209/pFG7 deposited under the accession No. DSM 12089.

* * * * *

SEQUENCE LISTING

<160> NUMBER OF SEQ ID NOS: 28

<210> SEQ ID NO 1
<211> LENGTH: 89
<212> TYPE: DNA
<213> ORGANISM: Artificial Sequence
<220> FEATURE:
<223> OTHER INFORMATION: Description of Artificial Sequence: DNA
      sequence comprising the tRNA encoding suppressor gene

<400> SEQUENCE: 1
ggagccatgg cagagtggta atgcaacgga ctctaaatcc gtcgaaccgt gtaaagcggc    60 gcagggttc aaatcccctt gactcctta                                      89

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 2
cgaattcata tttgattaat gagaatatgg aacc                               34

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
cgggatcctt tcaggaaggt aattaac                                       27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 4
cgaattcaac attttttgtat aaatatgcg                                    29

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 5
gggaattcag gaaggtaatt aactatgg                                      28

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 6
gcagatctaa gcttgattca agaagtaaaa gaaggc                             36

```
<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
atagatctac tcgatgccaa gaatggaccg c                              31

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (11)
<223> OTHER INFORMATION: a, t, c, g, other or unknown
<221> NAME/KEY: modified_base
<222> LOCATION: (14)
<223> OTHER INFORMATION: a, t, c, g, other or unknown
<221> NAME/KEY: modified_base
<222> LOCATION: (17)
<223> OTHER INFORMATION: a, t, c, g, other or unknown
<221> NAME/KEY: modified_base
<222> LOCATION: (20)
<223> OTHER INFORMATION: a, t, c, g, other or unknown

<400> SEQUENCE: 8
aaaggcctgt natngcnctn gayttycc                                  28

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (13)
<223> OTHER INFORMATION: a, t, c, g, other or unknown
<221> NAME/KEY: modified_base
<222> LOCATION: (16)
<223> OTHER INFORMATION: a, t, c, g, other or unknown

<400> SEQUENCE: 9
tggacgaatt ccnggngt                                             18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
catagtaaac gacttgggg                                            19

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11
tacgcacaaa aaaccgct                                             18
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 12
ggtcgccttt acttgcacc                                               19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
gattatattg ttgtcggccg                                              20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (24)
<223> OTHER INFORMATION: a, t, c, g, other or unknown

<400> SEQUENCE: 14
gctctagagc mwatygwwat dggn                                         24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (4)
<223> OTHER INFORMATION: a, t, c, g, other or unknown

<400> SEQUENCE: 15
ggtngartgg aaygaraara thaay                                        25

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
cctcaaccta ggagaaaatt atgc                                         24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17
tctcctaggt tgaggttaat tgtg                                         24

<210> SEQ ID NO 18

```
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
atagatctgc ttagaaaact tg                                          22

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
atagatctgc atgtaagcaa aaacc                                       25

<210> SEQ ID NO 20
<211> LENGTH: 12
<212> TYPE: PRT
<213> ORGANISM: Lactococcus lactis

<400> SEQUENCE: 20

Thr Gln Leu Thr Ser Thr Ser Glu Lys Ile Met Gln
 1               5                  10

<210> SEQ ID NO 21
<211> LENGTH: 36
<212> TYPE: DNA
<213> ORGANISM: Lactococcus lactis
<220> FEATURE:
<221> NAME/KEY: CDS
<222> LOCATION: (1)..(36)

<400> SEQUENCE: 21 aca caa tta acc tca act tct gag aaa att atg caa                   36
Thr Gln Leu Thr Ser Thr Ser Glu Lys Ile Met Gln
 1               5                  10

<210> SEQ ID NO 22
<211> LENGTH: 36
<212> TYPE: DNA
<213> ORGANISM: Lactococcus lactis
<220> FEATURE:
<221> NAME/KEY: CDS
<222> LOCATION: (1)..(18)

<400> SEQUENCE: 22 aca caa tta acc tca acc taggagaaaa ttatgcaa                       36
Thr Gln Leu Thr Ser Thr
 1               5

<210> SEQ ID NO 23
<211> LENGTH: 937
<212> TYPE: DNA
<213> ORGANISM: Lactococcus lactis
<220> FEATURE:
<221> NAME/KEY: CDS
<222> LOCATION: (224)..(934)

<400> SEQUENCE: 23
tgattttatt attagctaaa attactgaca gcctgtttaa tcattctgtc agtaaaatgc    60
gaccaaagcg agcattttat ccatagctaa aagaattgtc agcggagctg ataattctct   120
cgttcgttag cgaccaaagc gagcatttta tggatagcta aaagaattgt catcaaagct   180
```

-continued

```
gataattctg tcattaaata tttagaaaaa ggaagtagaa aaa atg caa gaa aat       235
                                              Met Gln Glu Asn
                                               1 aga cct gtc att gcc ctt gat ttc cct gaa ttc tca gac gta aaa gat       283
Arg Pro Val Ile Ala Leu Asp Phe Pro Glu Phe Ser Asp Val Lys Asp
  5              10                  15                  20 ttt ctc gaa aaa ttt gac ccg tca gaa caa ttg tat att aaa cta gga       331
Phe Leu Glu Lys Phe Asp Pro Ser Glu Gln Leu Tyr Ile Lys Leu Gly
              25                  30                  35 atg gaa ctt ttt tac acg gct ggg ccc caa gtc gtt tac tat gta aaa       379
Met Glu Leu Phe Tyr Thr Ala Gly Pro Gln Val Val Tyr Tyr Val Lys
          40                  45                  50 tcg ctc ggc cac agt gta ttc ctt gat tta aaa ctc cat gat att cca       427
Ser Leu Gly His Ser Val Phe Leu Asp Leu Lys Leu His Asp Ile Pro
      55                  60                  65 aac acc gtt gaa tcc tca atg cgt gtt tta gca cgt ttg gga ttg gat       475
Asn Thr Val Glu Ser Ser Met Arg Val Leu Ala Arg Leu Gly Leu Asp
   70                  75                  80 atg gtt aat gtt cac gcc gct ggt ggt gtt gaa atg atg gtt gca gct       523
Met Val Asn Val His Ala Ala Gly Gly Val Glu Met Met Val Ala Ala
 85                  90                  95                 100 aaa cgc ggt tta gag gct gga acg cca gtt gga cgg caa agg cca aaa       571
Lys Arg Gly Leu Glu Ala Gly Thr Pro Val Gly Arg Gln Arg Pro Lys
                105                 110                 115 tta att gcg gtc aca caa tta acc tca act tct gag aaa att atg caa       619
Leu Ile Ala Val Thr Gln Leu Thr Ser Thr Ser Glu Lys Ile Met Gln
                120                 125                 130 aat gac caa aaa att atg act agt ctt gaa gaa tcg gtt att aat tac       667
Asn Asp Gln Lys Ile Met Thr Ser Leu Glu Glu Ser Val Ile Asn Tyr
            135                 140                 145 gca caa aaa acc gct caa gca gga ctt gac ggt gtc gtt tgt tcg gca       715
Ala Gln Lys Thr Ala Gln Ala Gly Leu Asp Gly Val Val Cys Ser Ala
        150                 155                 160 cat gaa gtt gaa aaa att aaa gca gcg aca tcg aaa gaa ttc att tgt       763
His Glu Val Glu Lys Ile Lys Ala Ala Thr Ser Lys Glu Phe Ile Cys
165                 170                 175                 180 ctc aca cca gga att cgc cca gaa ggt gca agt aaa ggc gac caa aaa       811
Leu Thr Pro Gly Ile Arg Pro Glu Gly Ala Ser Lys Gly Asp Gln Lys
                185                 190                 195 cga gta atg aca cct aaa gaa gca aga aca att ggt tca gat tat att       859
Arg Val Met Thr Pro Lys Glu Ala Arg Thr Ile Gly Ser Asp Tyr Ile
                200                 205                 210 gtt gtc ggc cgt cca att acc caa gca aaa gat cca gta gct agc tat       907
Val Val Gly Arg Pro Ile Thr Gln Ala Lys Asp Pro Val Ala Ser Tyr
            215                 220                 225 cat gcg ata aaa gca gaa tgg aat caa taa                               937
His Ala Ile Lys Ala Glu Trp Asn Gln
        230                 235
```

<210> SEQ ID NO 24
<211> LENGTH: 237
<212> TYPE: PRT
<213> ORGANISM: Lactococcus lactis

<400> SEQUENCE: 24

```
Met Gln Glu Asn Arg Pro Val Ile Ala Leu Asp Phe Pro Glu Phe Ser
  1               5                  10                  15

Asp Val Lys Asp Phe Leu Glu Lys Phe Asp Pro Ser Glu Gln Leu Tyr
             20                  25                  30
```

```
Ile Lys Leu Gly Met Glu Leu Phe Tyr Thr Ala Gly Pro Gln Val Val
        35                  40                  45

Tyr Tyr Val Lys Ser Leu Gly His Ser Val Phe Leu Asp Leu Lys Leu
    50                  55                  60

His Asp Ile Pro Asn Thr Val Glu Ser Ser Met Arg Val Leu Ala Arg
 65                  70                  75                  80

Leu Gly Leu Asp Met Val Asn Val His Ala Ala Gly Gly Val Glu Met
                85                  90                  95

Met Val Ala Ala Lys Arg Gly Leu Glu Ala Gly Thr Pro Val Gly Arg
            100                 105                 110

Gln Arg Pro Lys Leu Ile Ala Val Thr Gln Leu Thr Ser Thr Ser Glu
        115                 120                 125

Lys Ile Met Gln Asn Asp Gln Lys Ile Met Thr Ser Leu Glu Glu Ser
    130                 135                 140

Val Ile Asn Tyr Ala Gln Lys Thr Ala Gln Ala Gly Leu Asp Gly Val
145                 150                 155                 160

Val Cys Ser Ala His Glu Val Glu Lys Ile Lys Ala Ala Thr Ser Lys
                165                 170                 175

Glu Phe Ile Cys Leu Thr Pro Gly Ile Arg Pro Glu Gly Ala Ser Lys
            180                 185                 190

Gly Asp Gln Lys Arg Val Met Thr Pro Lys Glu Ala Arg Thr Ile Gly
        195                 200                 205

Ser Asp Tyr Ile Val Val Gly Arg Pro Ile Thr Gln Ala Lys Asp Pro
    210                 215                 220

Val Ala Ser Tyr His Ala Ile Lys Ala Glu Trp Asn Gln
225                 230                 235

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Vector
      pFG100

<400> SEQUENCE: 25
ggtaccgggc cccccctcga ggtcgacggt atcgataagc ttgatatcga attc          54

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Vector
      pFG100

<400> SEQUENCE: 26
ggatccacta gttctagagc ggccgccacc gcggtggagc tccagc                  46

<210> SEQ ID NO 27
<211> LENGTH: 69
<212> TYPE: DNA
<213> ORGANISM: Artificial Sequence
<220> FEATURE:
<223> OTHER INFORMATION: Description of Artificial Sequence: Vector
      pFG200

<400> SEQUENCE: 27
gaattcatcg atatctagat ctcgagctcg cgaaagcttg gctgcaggtc gacggatccc   60
cgggaattc                                                          69
```

```
<210> SEQ ID NO 28
<211> LENGTH: 6
<212> TYPE: PRT
<213> ORGANISM: Lactococcus lactis

<400> SEQUENCE: 28

Thr Gln Leu Thr Ser Thr
  1               5
```